United States Patent
Okita

(10) Patent No.: US 11,471,030 B2
(45) Date of Patent: Oct. 18, 2022

(54) VARIABLE STIFFNESS DEVICE, VARIABLE STIFFNESS SYSTEM, ENDOSCOPE, AND STIFFNESS VARYING METHOD

(71) Applicant: OLYMPUS CORPORATION, Tokyo (JP)

(72) Inventor: Tatsuhiko Okita, Akiruno (JP)

(73) Assignee: OLYMPUS CORPORATION, Tokyo (JP)

( * ) Notice: Subject to any disclaimer, the term of this patent is extended or adjusted under 35 U.S.C. 154(b) by 237 days.

(21) Appl. No.: 16/869,632

(22) Filed: May 8, 2020

(65) Prior Publication Data
US 2020/0260934 A1 Aug. 20, 2020

Related U.S. Application Data

(63) Continuation of application No. PCT/JP2017/041533, filed on Nov. 17, 2017.

(51) Int. Cl.
*A61B 1/005* (2006.01)
*A61B 1/015* (2006.01)
*A61B 1/12* (2006.01)

(52) U.S. Cl.
CPC .......... *A61B 1/0058* (2013.01); *A61B 1/0055* (2013.01); *A61B 1/015* (2013.01); *A61B 1/128* (2013.01)

(58) Field of Classification Search
CPC ........ A61B 1/0058; A61B 1/015; A61B 1/128
See application file for complete search history.

(56) References Cited

U.S. PATENT DOCUMENTS 5,019,040 A * 5/1991 Itaoka .................... A61B 18/26
604/20
5,645,520 A * 7/1997 Nakamura ........... A61B 1/0058
600/153

(Continued)

FOREIGN PATENT DOCUMENTS

WO 2012/043034 A1 4/2012
WO 2017/094085 A1 6/2017

(Continued)

OTHER PUBLICATIONS

Hirose, S. et al., "Development of Shape Memory Alloy Actuator (Characteristics Measurements of the Alloy and Development of an Active Endoscope)", Journal of the Robotics Society of Japan, vol. 5, No. 2, pp. 3-17, Apr. 1987.

(Continued)

*Primary Examiner* — Aaron B Fairchild
(74) *Attorney, Agent, or Firm* — Scully, Scott, Murphy & Presser, P.C.

(57) ABSTRACT

A variable stiffness device includes a shape-memory unit formed of at least two hollow shape-memory members connected together. Each of the shape-memory members is transitionable in phase between a first phase in which the shape-memory member is in a low stiffness state and a second phase in which the shape-memory member is in a high stiffness state. The shape-memory member in the high stiffness state has a higher level of stiffness than in the low stiffness state. Hollow portions of the shape-memory members are connected together so that the shape-memory unit has a lumen-like inner space configured to allow fluid for cooling the shape-memory members to flow. The variable stiffness device also includes a heating member configured to heat the shape-memory members.

14 Claims, 11 Drawing Sheets

(56) References Cited

U.S. PATENT DOCUMENTS

| | | | |
|---|---|---|---|
| 2002/0013550 A1 | 1/2002 | Unsworth et al. | |
| 2018/0263468 A1* | 9/2018 | Morishima | A61B 1/0058 |
| 2018/0266402 A1* | 9/2018 | Takahashi | F03G 7/065 |
| 2019/0046008 A1* | 2/2019 | Morishima | A61B 1/0058 |
| 2019/0046010 A1 | 2/2019 | Tojo et al. | |

FOREIGN PATENT DOCUMENTS

| | | |
|---|---|---|
| WO | 2017/183078 A1 | 10/2017 |
| WO | 2017179126 A1 | 10/2017 |

OTHER PUBLICATIONS

International Search Report dated Feb. 6, 2018 issued in International Application No. PCT/JP2017/041533.

English translation of International Preliminary Report on Patentability dated May 28, 2020, together with the Written Dpinion received in related International Application No. PCT/JP2017/041533.

Japanese Office Action dated Dec. 22, 2020 received in 2019-554151.

\* cited by examiner

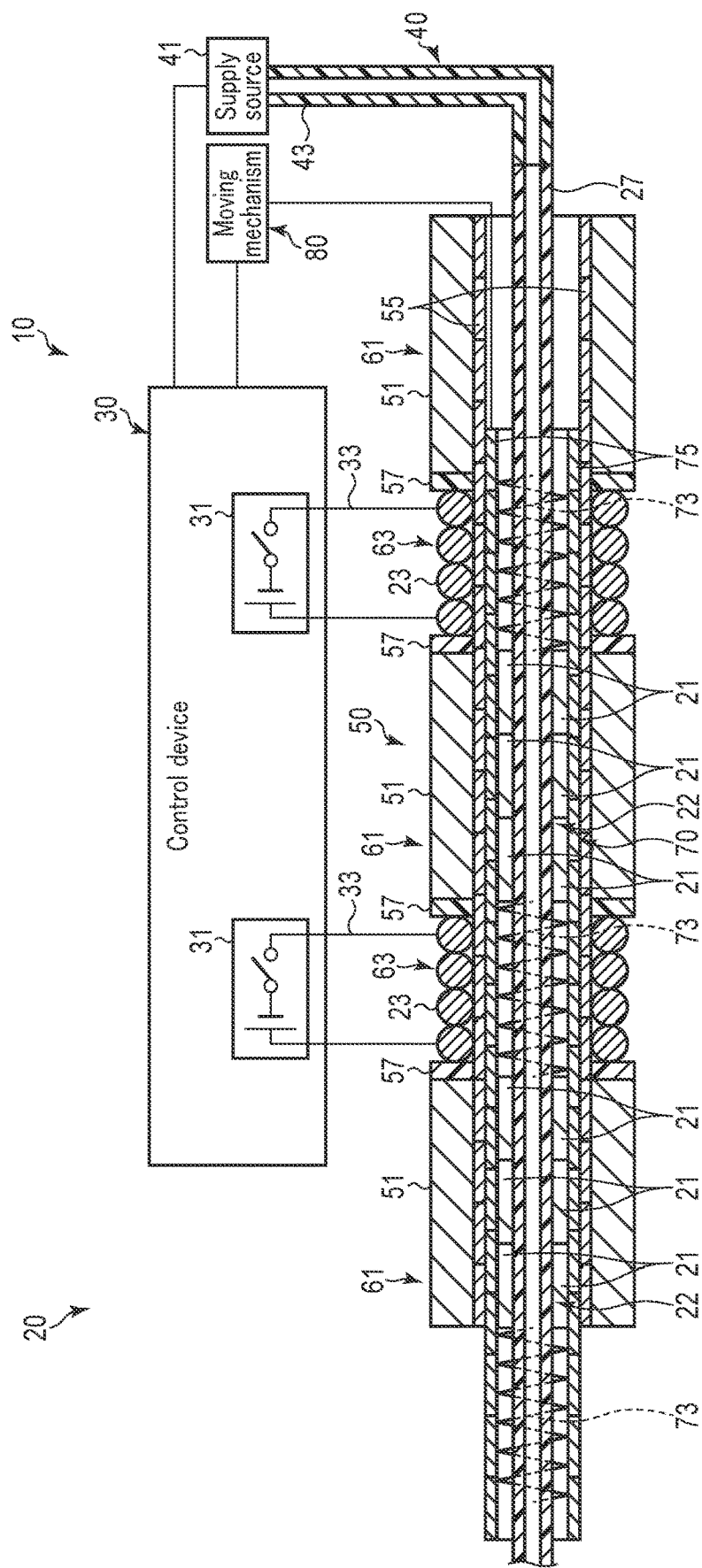
F I G. 10A

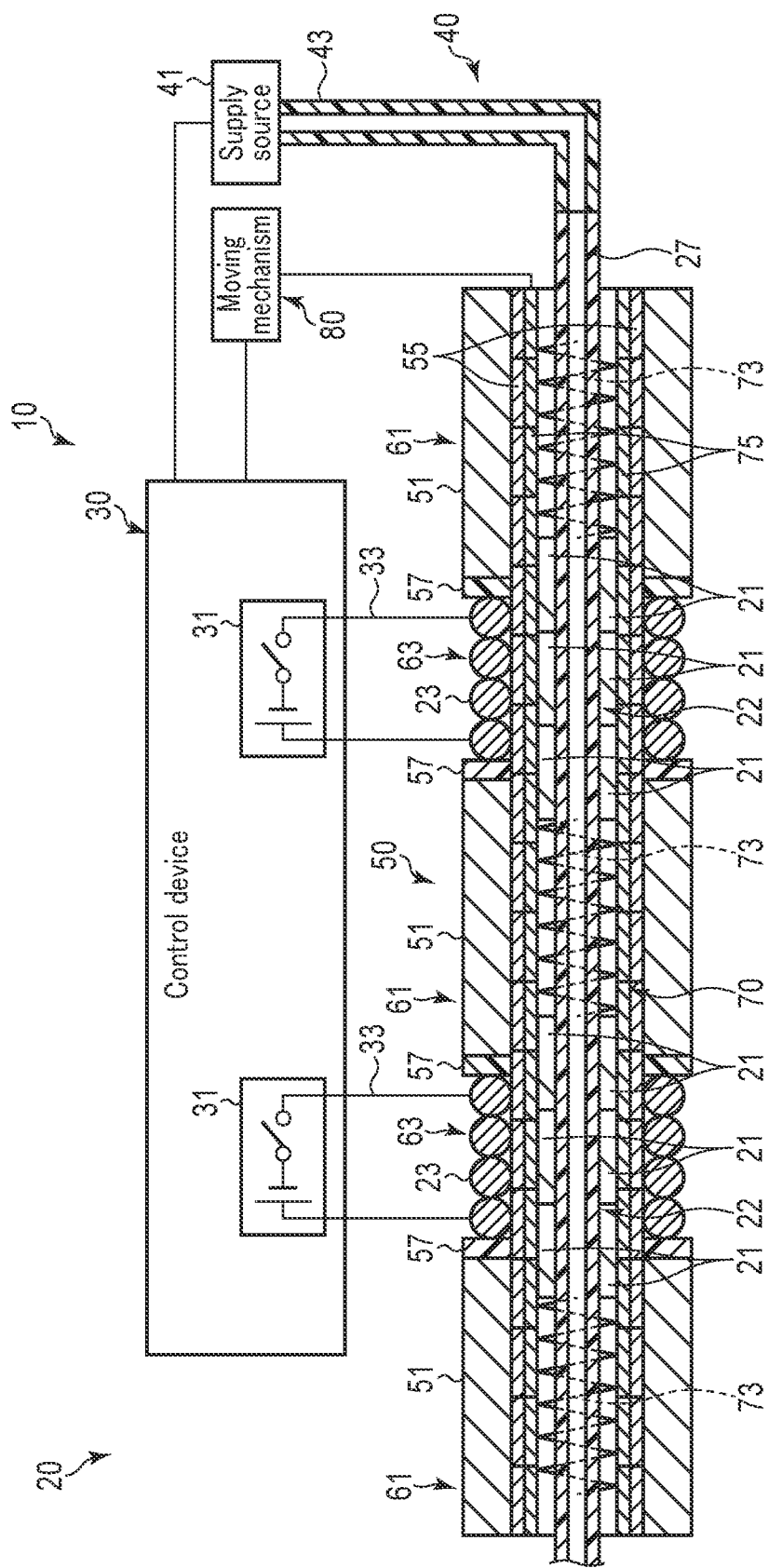
F I G. 10B

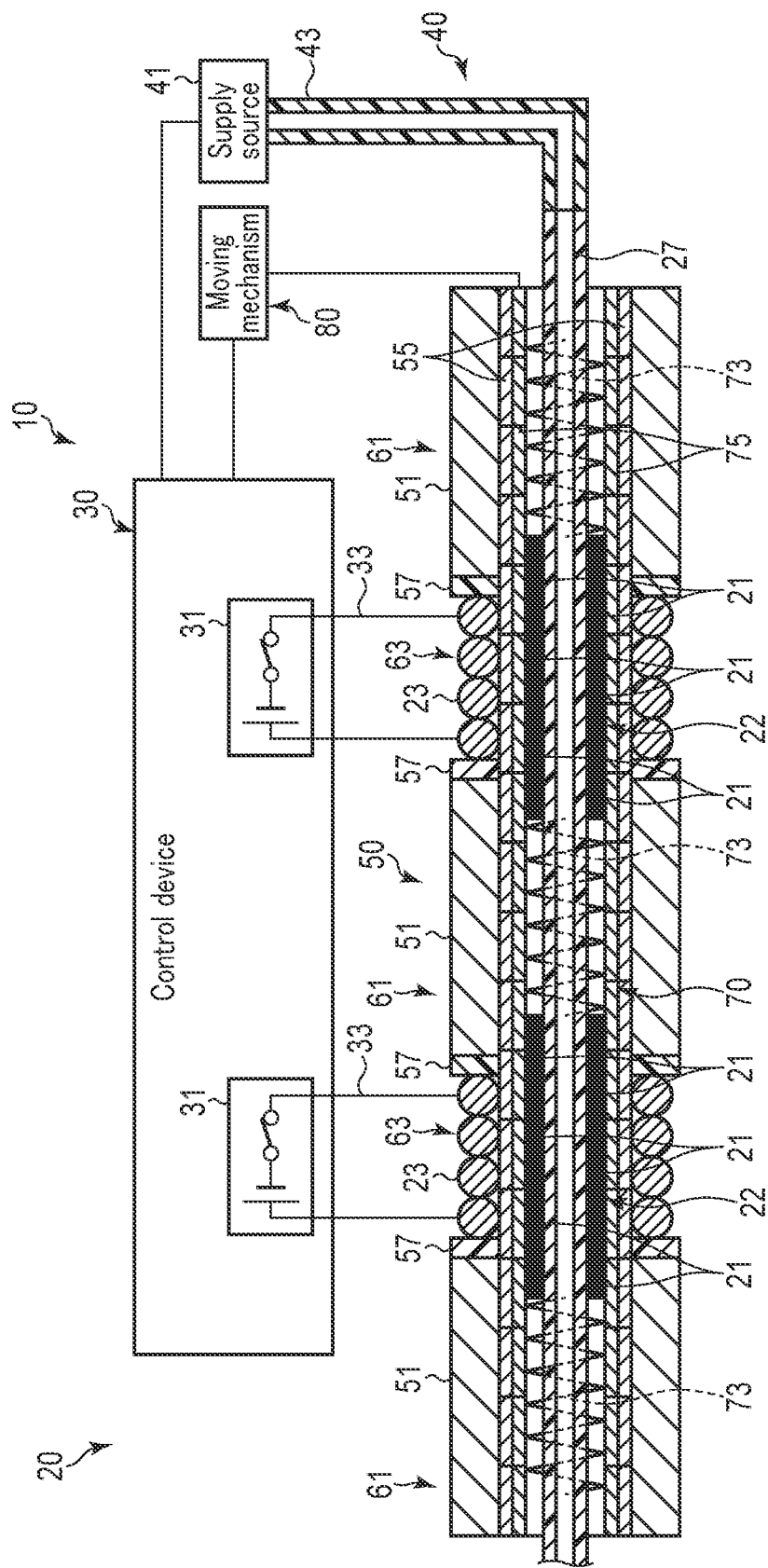
F I G. 10C

VARIABLE STIFFNESS DEVICE, VARIABLE STIFFNESS SYSTEM, ENDOSCOPE, AND STIFFNESS VARYING METHOD

CROSS-REFERENCE TO RELATED APPLICATIONS

This application is a Continuation Application of PCT Application No. PCT/JP2017/041533, filed Nov. 17, 2017, the entire contents of which are incorporated herein by reference.

BACKGROUND OF THE INVENTION

1. Field of the Invention

The present invention relates to a variable stiffness device configured to provide a flexible member with different levels of stiffness, a variable stiffness system including the variable stiffness device, an endoscope including the variable stiffness device, and a stiffness varying method for the variable stiffness device.

2. Description of the Related Art

For example, International Publication No. 2017/094085 discloses a variable rigidity actuator to be installed in a flexible member to provide the flexible member with different levels of rigidity. The variable rigidity actuator includes a shape-memory member transitionable in phase between a first phase and a second phase, a heating member configured to cause the phase of the shape-memory member to transition between the first phase and the second phase, and a cooling system configured to cool the shape-memory member. When the phase of the shape-memory member is the first phase, the shape-memory member is in a soft state in which the shape-memory member can easily be deformed in response to an external force to provide the flexible member with a low level of rigidity. When the phase of the shape-memory member is the second phase, the shape-memory member is in a hard state in which the shape-memory member tends to assume its memorized shape against the external force to provide the flexible member with a high level of rigidity. The cooling system includes heat transfer media for facilitating at least part of heat dissipation for the shape-memory member.

The shape-memory member made of a shape memory alloy has a hollow form and located in an elongate flexible member.

BRIEF SUMMARY OF THE INVENTION

An aspect of a variable stiffness device according to the present invention includes a shape-memory unit formed of at least two hollow shape-memory members connected together. Each of the shape-memory members is transitionable in phase between a first phase in which the shape-memory member is in a low stiffness state and a second phase in which the shape-memory member is in a high stiffness state. The shape-memory member in the high stiffness state has a higher level of stiffness than in the low stiffness state. Hollow portions of the shape-memory members are connected together so that the shape-memory unit has a lumen-like inner space configured to allow fluid for cooling the shape-memory members to flow. The variable stiffness device also includes a heating member configured to heat the shape-memory members.

An aspect of a variable stiffness system according to the present invention includes the aforementioned variable stiffness device, a control device configured to control the heating member for heating, and a cooling system configured to supply the fluid to the shape-memory unit.

An aspect of an endoscope according to the present invention includes the aforementioned variable stiffness device, and a flexible member in which the variable stiffness device is installed.

An aspect of a variable stiffness device according to the present invention includes a first elongated member, and a second elongated member movable along the first elongated member. The first elongated member includes: a high bending stiffness section including at least one hard member, and a low bending stiffness section adjacent to the at least one hard member; the low bending stiffness section including a heating member configured to heat the second elongated member. The second elongated member includes: at least one shape-memory unit formed of at least two hollow shape-memory members, each of the shape-memory members being transitionable in phase between a first phase in which the shape-memory member is in a low stiffness state and a second phase in which the shape-memory member is in a high stiffness state on heating by the heating member, the shape-memory member in the high stiffness state having a higher level of stiffness than in the low stiffness state, hollow portions of the shape-memory members being connected together so that the shape-memory unit has a lumen-like inner space configured to allow fluid for cooling the shape-memory members to flow; and a soft member adjacent to the at least one shape-memory unit, the soft member being softer than the low bending stiffness section and being in a hollow form in which the fluid flows, an inner space of the soft member being connected to the inner space of the shape-memory unit.

An aspect of a variable stiffness system according to the present invention includes the abovementioned variable stiffness device, a control device configured to control the heating member for heating, and a cooling system configured to supply the fluid to the shape-memory unit.

An aspect of an endoscope according to the present invention includes the abovementioned variable stiffness device, and a flexible member in which the variable stiffness device is installed.

An aspect according to the present invention is directed to a stiffness varying method for a variable stiffness device that includes: a shape-memory unit formed of at least two hollow shape-memory members connected together, each of the shape-memory members being transitionable in phase between a first phase in which the shape-memory member is in a low stiffness state and a second phase in which the shape-memory member is in a high stiffness state, the shape-memory member in the high stiffness state having a higher level of stiffness than in the low stiffness state, hollow portions of the shape-memory members being connected together so that the shape-memory unit includes a lumen-like inner space; and a heating member. The method includes heating the shape-memory members by the heating member, and cooling the shape-memory members by causing fluid to flow in the lumen-like inner space.

Advantages of the invention will be set forth in the description that follows, and in part will be obvious from the description, or may be learned by practice of the invention. The advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 10A is a schematic view of a variable stiffness system according to a sixth embodiment of the present invention, illustrating the variable stiffness device of the variable stiffness system being in a lowest stiffness state.

FIG. 10B illustrates that the variable stiffness device illustrated in FIG. 10A is switched from the lowest stiffness state to a low stiffness state.

FIG. 10C illustrates that the variable stiffness device illustrated in FIG. 10B is switched from the low stiffness state to a high stiffness state.

DETAILED DESCRIPTION OF THE INVENTION

Hereinafter, embodiments of the present invention will be described with reference to the drawings. In some drawings, part of the members is not shown so as to clarify the illustration.

First Embodiment

Figure 1:
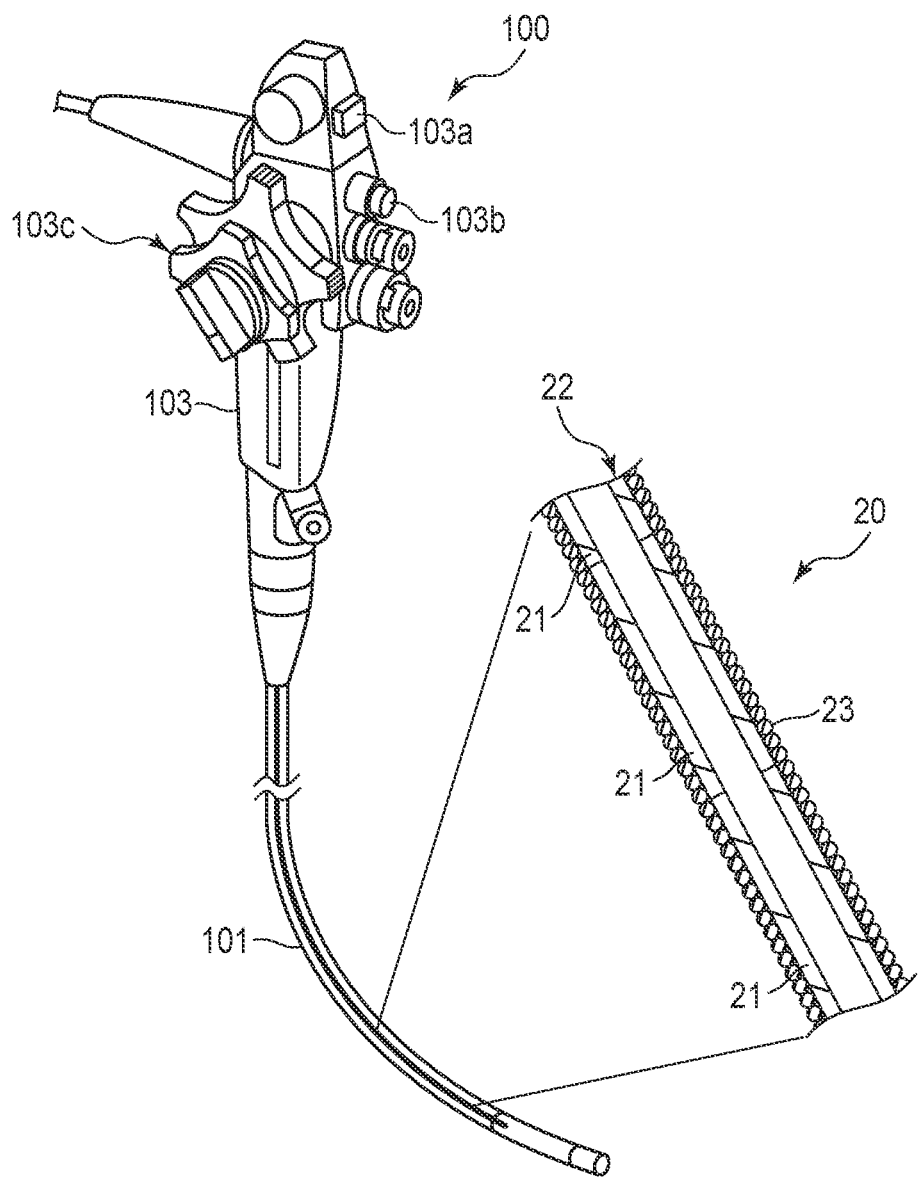
FIG. 1 is a perspective view of an endoscope in which a variable stiffness device of a variable stiffness system according to a first embodiment of the present invention is incorporated.
Figure 2:
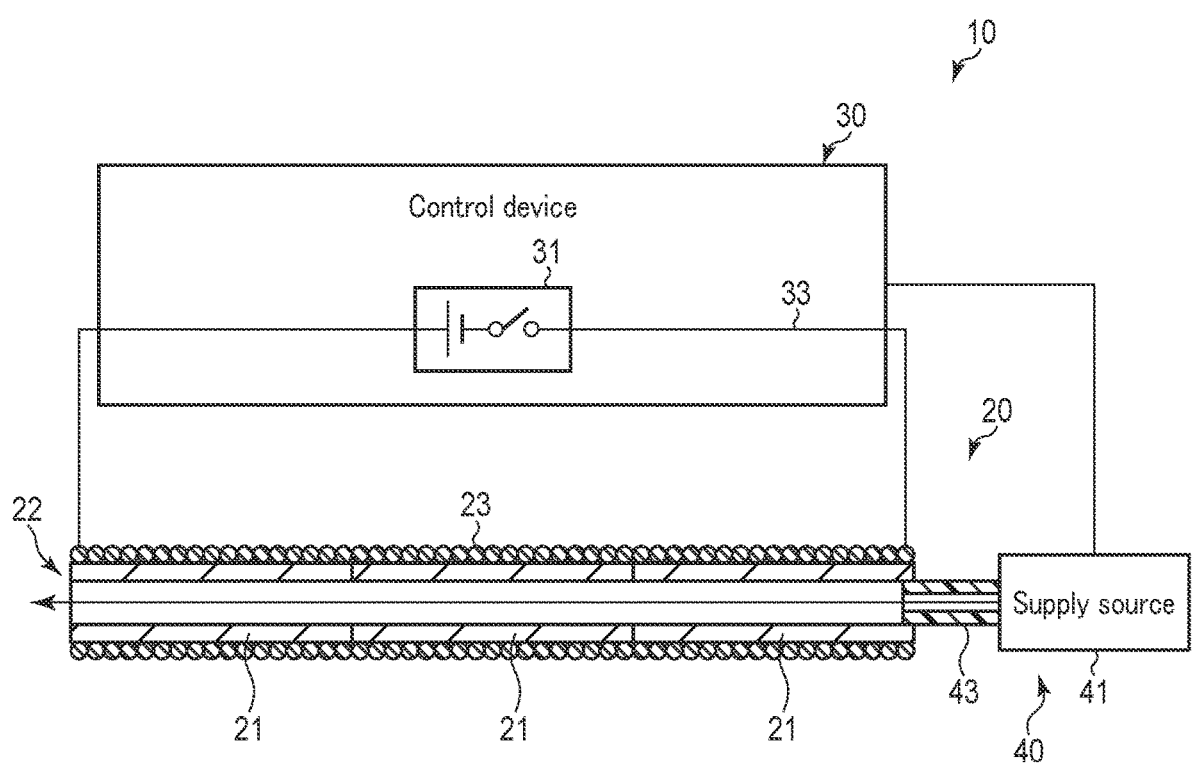
FIG. 2 is a schematic view of the variable stiffness system illustrated in FIG. 1.

A first embodiment of the present invention will now be described with reference to FIG. 1 and FIG. 2. FIG. 1 is a perspective view of an endoscope 100 in which a variable stiffness device 20 of a variable stiffness system 10 according to the first embodiment is incorporated. FIG. 2 is a schematic view of the variable stiffness system 10 illustrated in FIG. 1.

The endoscope 100 may be for a medical purpose or an industrial purpose. The endoscope 100 includes a flexible member 101, a control section 103 connected to a proximal end of the flexible member 101, and a variable stiffness device 20 installed in the flexible member 101.

The flexible member 101 is an elongate tube. The flexible member 101 is provided with a camera at a distal end thereof. The flexible member 101 is adapted to be inserted into a subject. The camera can take an image inside the subject. The flexible member 101 can be bent by an external force applied to the flexible member 101. As for the external force, gravity is also taken into consideration as part of the external force.

The control section 103 includes switches 103a, 103b and a control dial 103c that are used to perform various operations on the endoscope 100.

The endoscope 100 of the present embodiment is provided with the variable stiffness device 20 configured to vary the stiffness of the flexible member 101 within the flexible member 101. The variable stiffness device 20 may be located along part of the entire length of the flexible member 101 or may be located along the entire length of the flexible member 101.

As illustrated in FIG. 2, the variable stiffness system 10 includes the variable stiffness device 20 configured to provide the flexible member 101 with different levels of stiffness, a control device 30 configured to control stiffness of the variable stiffness device 20, and a cooling system 40 configured to cool a shape-memory unit 22 of the variable stiffness device 20.

The variable stiffness device 20 includes at least two hollow shape-memory members 21, and a coiled heating member 23 wound around the outer periphery of the shape-memory members 21.

The shape-memory members 21 are connected together in the longitudinal direction of the shape-memory members 21 to form an elongate tubular shape-memory unit 22 in its entirety. Specifically, adjacent ends of adjacent shape-memory members 21 may be directly connected to each other by bonding, welding, or the like. For example, bonding or welding is performed all around the outer peripheral surface of the ends of the shape-memory members 21. Three shape-memory members 21, each of which serves as a short pipe, are connected, so as to function as one long tubular shape-memory unit 22. The shape-memory unit 22 has a lumen-like inner space formed of hollow portions of the shape-memory members 21 connected together. The inner space is configured to allow fluid to flow for cooling the shape-memory members 21. Although FIG. 2 illustrates an example in which three shape-memory members 21 are arranged for simplicity of illustration, there only needs to be two or more shape-memory members 21.

The shape-memory member 21 is, for example, in a cylindrical shape. For example, the outer diameter of the shape-memory member 21 is smaller than the inner diameter of the flexible member 101. The shape-memory unit 22 is shorter than the flexible member 101.

The shape-memory member 21 may be any member that causes transformation in phase of the shape-memory member 21 in accordance with temperature and exhibits large variation in stiffness caused by the transformation. Such a shape-memory member 21 may be made of a shape memory alloy, for example. The shape memory alloy may be any alloy including NiTi or NiTiCu, for example. The shape-memory member 21 may be made of other materials such as shape-memory polymer, shape-memory gel, or shape-memory ceramics.

The shape memory alloy constituting the shape-memory member 21 may be any alloy transitionable in phase between, for example, a martensitic phase and an austenitic phase. The shape memory alloy is plastically deformable relatively easily in the martensitic phase in response to an external force. In other words, the shape memory alloy exhibits low modulus of elasticity in the martensitic phase. On the other hand, the shape memory alloy is not deformable easily in the austenitic phase against the external force. Consider here that the shape memory alloy deforms due to a larger external force. When the larger external force on the deformed shape memory alloy is cancelled out, the shape memory alloy exhibits superelasticity and returns to the shape that is memorized. In other words, the shape memory alloy exhibits high modulus of elasticity in the austenitic phase.

The phase in which the shape-memory member 21 exhibits low modulus of elasticity will be referred to as a first phase and the phase in which the shape-memory member 21 exhibits high modulus of elasticity will be referred to as a second phase. The phase of the shape-memory member 21 can vary between the first phase and the second phase by heating or cooling.

When the phase of the shape-memory member 21 is the first phase, the shape-memory member 21 is in a low stiffness state in which the shape-memory member 21 can easily be deformed in response to an external force, that is, it exhibits low modulus of elasticity. Accordingly, the phase of the shape-memory member 21 is the first phase, the variable stiffness device 20 provides a flexible member 101 with a relatively low level of stiffness by the shape-memory member 21. For example, the low stiffness refers to such stiffness that the flexible member 101 is easily to bend. In the first phase, for example, the variable stiffness device 20 and the flexible member 101 can easily be bent by an external force.

When the phase of the shape-memory member 21 is the second phase, the shape-memory member 21 is in a high stiffness state in which the shape-memory member 21 has higher stiffness than in the low stiffness state, and exhibits a high modulus of elasticity. In the high stiffness state, the shape-memory member 21 tends to assume its memorized shape, which is memorized in advance, against the external force. The memorized shape may, for example, be substantially linear. Accordingly, when the phase of the shape-memory member 21 is the second phase, the variable stiffness device 20 provides the flexible member 101 with a relatively high level of stiffness by the shape-memory member 21. For example, the high stiffness refers to such stiffness that the flexible member 101 is less easily to bend, or such stiffness that the flexible member 101 maintains the substantially linear state against the external force. In the second phase, for example, the variable stiffness device 20 and the flexible member 101 can maintain the substantially linear state, or can be bent more gradually than in the first phase even with the external force.

In order to vary the phase of the shape-memory member 21 between the first phase and the second phase, the variable stiffness system 10 is provided with the heating member 23 and the cooling system 40. The shape-memory member 21 has a property to transition in phase from the first phase to the second phase on heating by the heating member 23. The shape-memory member 21 also has a property to transition in phase from the second phase to the first phase on cooling by the cooling system 40. In other words, the heating member 23 and the cooling system 40 cause a transition in phase of the shape-memory member 21 between the first phase and the second phase to vary the stiffness state of the shape-memory member 21.

The heating member 23 includes, for example, a spiral coil member such as a tightly-wound coil. The coil member of the heating member 23 may be a loosely-wound coil. The coil member is a wire-like member. The heating member 23 is located along the entire length of the shape-memory unit 22.

The heating member 23 is made of a conductive material and may be made of, for example, a heating wire, that is, a conductive member that has a large electric resistance. The heating member 23 has an ability to generate heat upon supply of an electric current from the control device 30. The control device 30 includes a driver 31 configured to drive the heating member 23. The driver 31 includes a power supply and a switch. The driver 31 is electrically connected to the heating member 23 through the wiring 33. The wiring 33 is, for example, a wire-like metal member. The wiring 33 only needs to be electrically connected to the heating member 23, and may be integral with the heating member 23 or may be separate from the heating member 23. The driver 31 supplies an electric current to the heating member 23 through the wiring 33 in response to the switch being operated to on. In this way, the heating member 23 generates heat. The calorific value of the heating member 23 depends on the supply of the electric current. The heating member 23 transfers the heat to the shape-memory unit 22 arranged around the heating member 23. The heating member 23 then causes a transition in phase of the shape-memory unit 22 from the first phase to the second phase by heat. The heating member 23 functions as a heater. The temperature of the heat is, for example, in the range from 70 to 80 degrees Centigrade. The driver 31 stops supplying the electric current to the heating member 23 in response to the switch being operated to off. In this way, the heating member 23 stops generating heat.

The heating member 23 may be located in any location where a transition in phase of the shape-memory unit 22 can be caused. Accordingly, for example, the heating member 23 is arranged around the outside of the shape-memory unit 22. The heating member 23 extends along the longitudinal axis of the shape-memory unit 22. The heating member 23 extends spirally around the shape-memory unit 22 along the longitudinal axis of the shape-memory unit 22. Consequently, the shape-memory unit 22 is located inside the winding of the heating member 23. The heating member 23 is in close contact with the outer peripheral surface of the shape-memory unit 22; however, the heating member 23 may be spaced apart from the outer peripheral surface of the shape-memory unit 22 by a suitable clearance. With the configuration, the heat emitted by the heating member 23 is efficiently transferred to the shape-memory unit 22, which leads to a thinner variable stiffness device 20.

The the variable stiffness system 10 includes only one heating member 23 arranged with respect to the entire shape-memory unit 22, and the heating member 23 causes a transition in phase of three shape-memory members 21 in a substantially simultaneous manner. Such a configuration leads to a simple configuration of the variable stiffness device 20. It will be noted that the heating member 23 may be divided and arranged for each shape-memory member 21.

For example, a first insulation film (not shown) is arranged around the shape-memory member 21. The first insulation film prevents shorting between the shape-memory member 21 and the heating member 23. The first insulation film covers at least a portion facing the heating member 23. Accordingly, the first insulation film may be arranged to partially cover the outer peripheral surface of the shape-memory member 21 or may be arranged over the entire outer peripheral surface of the shape-memory member 21.

For example, a second insulation film (not shown) is provided around the heating member 23. The second insulation film serves to prevent shorting between the shape-memory member 21 and the heating member 23.

The cooling system 40 supplies cooling fluid to the inner space of the shape-memory unit 22 formed of hollow portions of the shape-memory members 21 connected together to cool the shape-memory unit 22. Cooling as used herein refers at least to facilitating heat dissipation of the shape-memory unit 22, or an object of interest, or in other words, enhancing heat dissipation effects of the object of interest.

The cooling system 40 includes a supply source 41 configured to supply cooling fluid to the shape-memory unit 22 and a conduit member 43 configured to direct the fluid flowing out of the supply source 41 to the shape-memory unit 22.

The fluid is gas or liquid. The fluid is, for example, cooling media the temperature of which is adjusted to a temperature lower than that of the shape-memory unit 22 in the second phase. The temperature of the fluid is, for example, 38 degrees Centigrade. The temperature of the fluid may be the ordinary temperature, or may be substantially the same temperature as that in a room in which the endoscope 100 is used, such as an operating room or a laboratory.

The supply source 41 is connected to the shape-memory unit 22 by the conduit member 43. The supply source 41 includes, for example, a compressor or a pump. The supply source 41 may have a function of controlling the temperature of the fluid, the supply of the fluid, and a supply time duration of the fluid as desired.

The conduit member 43 is, for example, a tube of a resin material or a metal material. The conduit member 43 is connected to the shape-memory unit 22. For example, the conduit member 43 is inserted into an end of the shape-memory unit 22. The end of the shape-memory unit 22 may instead be inserted into the conduit member 43. The conduit member 43 directs fluid to the inner space of the shape-memory unit 22 in a hollow form. Since no member is located in the inner space of the shape-memory unit 22, the fluid directed to the inner space of the shape-memory unit 22 flows in the inner space of the shape-memory unit 22 while being in direct contact with the inner peripheral surface of the shape-memory unit 22. The inner peripheral surface of the shape-memory unit 22 may be covered with a protection film or the like.

The control device 30 and the cooling system 40 may be mounted on the endoscope 100, or may be mounted on a control device (not shown) for the endoscope 100 connected to the endoscope 100. Accordingly, the variable stiffness system 10 is mounted on the endoscope 100, or mounted on an endoscope system including the endoscope 100 and the control device for the endoscope 100. For example, the switch 103a of the endoscope 100 functions as a switch for the driver 31 of the control device 30. Further, the switch 103b of the endoscope 100 functions as a switch for the supply source 41 of the cooling system 40. The control device 30 controls the supply source 41 to be driven in response to the switch 103b being operated to on or off. The control device 30 is, for example, made up of a hardware circuit including an ASIC or the like. The control device 30 may be made up of a CPU. When the control device 30 is made up of a processor, an internal memory in the processor or an external memory (not shown) arranged to be accessible to the processor includes program codes stored therein, which when executed by the processor, causes the processor to function as the control device 30.

Varying the stiffness of the flexible member 101 upon switching of the phase will now be described.

In the initial state of the variable stiffness system 10, the switch of the driver 31 is in an off state, the driver 31 does not supply an electric current to the heating member 23, and thus the heating member 23 does not generate heat. The phase of the shape-memory unit 22 is the first phase, and the shape-memory unit 22 is in a low stiffness state. The variable stiffness device 20 thereby provides a relatively low level of stiffness to the flexible member 101 by means of the shape-memory unit 22. For example, the flexible member 101 is thereby easily bendable by an external force applied to the flexible member 101.

When the switch of the driver 31 is turned on, the driver 31 supplies an electric current to the heating member 23, causing the heating member 23 to generate heat. Then, the heat is transferred from the heating member 23 to the shape-memory unit 22. The shape-memory unit 22 is heated by the heat, and the phase of the shape-memory unit 22 is rapidly switched from the first phase to the second phase by the heat. In this way, the shape-memory unit 22 experiences a variation from the low stiffness state to the high stiffness state. The variable stiffness device 20 provides a relatively high level of stiffness to the flexible member 101 by means of the shape-memory unit 22. Then, the flexible member 101 can maintain the substantially linear state, or can be bent more gradually than in the first phase even with the external force, for example.

The phase of the shape-memory unit 22 is returned from the second phase to the first phase as follows. First, the switch of the driver 31 is turned off, the driver 31 stops supplying the electric current to the heating member 23, and the heating member 23 stops generating heat. Then, the supply source 41 supplies fluid to the shape-memory unit 22.

The fluid flowing out of the supply source 41 passes through the conduit member 43 into the inner space of the shape-memory unit 22 and then passes through the inner space of the shape-memory unit 22 as indicated by an arrow in FIG. 2. The fluid flows in the inner space while being in contact with the inner peripheral surface of the shape-memory unit 22. The heat in the shape-memory unit 22 is transferred to the fluid, and passes through inner space of the shape-memory unit 22 with the fluid. The fluid passed through the inner space of the shape-memory unit 22 may be stored, may be discarded, or may be circulated for reuse and cooling. The cooling system 40 supplies fluid to the inner space of the shape-memory unit 22 to cool the shape-memory unit 22 to a desired temperature. The desired temperature refers for example to a temperature at which the phase of the shape-memory unit 22 becomes the first phase.

While fluid is supplied to the inner space of the shape-memory unit 22, the temperature of the shape-memory unit 22 decreases faster than while fluid is not supplied to the inner space of the shape-memory unit 22. In other words, the shape-memory unit 22 is cooled more rapidly than natural cooling.

Since the phase of the shape-memory unit 22 is rapidly switched between the first phase and the second phase, the stiffness in an area of the flexible member 101 in which the variable stiffness device 20 is located is rapidly switched.

In the present embodiment, instead of being formed from one elongate hollow shape-memory member 21, the shape-memory unit 22 is formed of thin and short hollow shape-memory members 21 connected to each other. It is less difficult to shape short shape-memory members 21 than to shape one elongate shape-memory member 21 into a hollow form. Further, it is relatively easy to connect shape-memory members 21 to each other by bonding, welding, or the like. Therefore, fabrication of the shape-memory unit 22 according to the present embodiment is relatively easy.

In the present embodiment, when the flexible member 101 is switched from the low stiffness state to the high stiffness state, high response to switching can be achieved by transferring heat to the shape-memory unit 22. Further, in the present embodiment, the shape-memory unit 22 can be cooled more rapidly than natural cooling by the cooling system 40, and thus high response to switching can be achieved when the flexible member 101 is switched from the high stiffness state to the low stiffness state.

Since the inner space of the shape-memory unit 22 in which cooling fluid flows is formed of three hollow shape-memory members 21 being connected together, no other member for causing the fluid to flow is located in the inner space of the shape-memory unit 22. It is therefore possible to provide a thin shape-memory unit 22. Further, since the fluid is in direct contact with the inner peripheral surface of the shape-memory unit 22, a great cooling effect can be achieved.

In this description, although the variable stiffness device 20 located on the flexible member 101 has been described as an example, the present embodiment is not limited thereto. The variable stiffness device 20 may, for example, be located on other elongate members such as a manipulator and a catheter.

Second Embodiment

Figure 3:
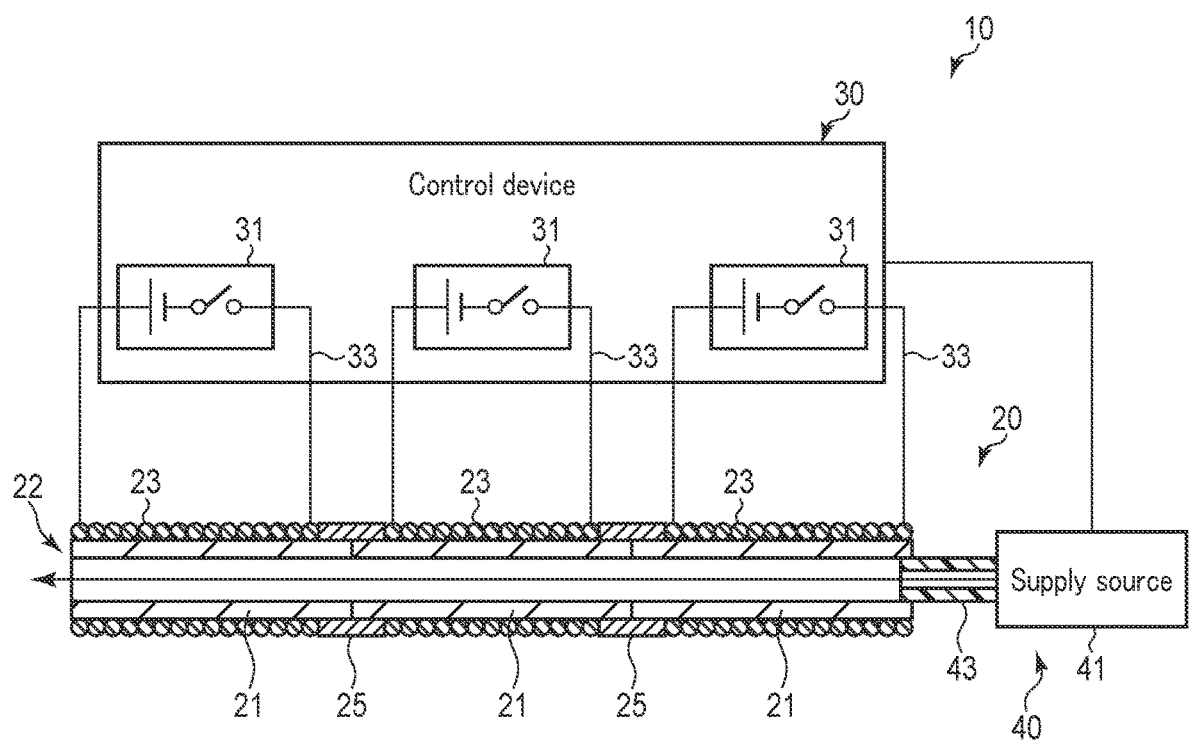
FIG. 3 is a schematic view of a variable stiffness system according to a second embodiment of the present invention.

A second embodiment of the present invention will now be described with reference to FIG. 3. FIG. 3 is a schematic view of a second embodiment of the variable stiffness system. In the present embodiment, differences in the second embodiment from the first embodiment will be emphasized.

In the present embodiment, for connection, the shape-memory unit 22 includes cylindrical connecting members 25 configured to connect adjacent shape-memory members 21 in the longitudinal direction of the variable stiffness device 20.

The connecting member 25 is, for example, in a cylindrical shape. The connecting member 25 is a pipe shorter than the shape-memory member 21. The outer diameter of the connecting member 25 may be substantially the same as the outer diameter of the winding of the heating member 23.

The connecting member 25 has a property to unbend and return to an original state, for example to a substantially linear state, when an external force is removed after the connecting member 25 is bent by the external force. The connecting member 25 may, for example, be of a metal material such as NiTi. The connecting member 25 may be formed of a member that is less easily to be bent by an external force. Such a member may, for example, be of a metal material such as stainless steel. The connecting member 25 may have a desired resiliency. The resiliency includes, for example, bounce, springiness, toughness, and the like, and causes a bent connecting member 25 to return to substantially linear in nature.

The connecting member 25 is located at adjacent ends of adjacent shape-memory members 21, which are connecting portions of the shape-memory members 21. In the longitudinal direction of the variable stiffness device 20, the adjacent shape-memory members 21 are each located within the connecting member 25 so as to come into contact with each other. Specifically, adjacent ends of adjacent shape-memory members 21 are inserted at opposite ends of the connecting member 25 into the connecting member 25 and directly connected by the connecting member 25. The connecting member 25 is located on the outer peripheries of the shape-memory members 21 and serves as an outer connecting member to externally connect the shape-memory members 21.

The heating member 23 and the driver 31 may be arranged for each of three shape-memory members 21. The heating members 23 are electrically insulated from each other and each of the drivers 31 individually drives the heating member 23. In this way, the phase of each of three shape-memory members 21 is allowed to individually transition from the first phase to the second phase, and the stiffness of the variable stiffness device 20 can be partially variable.

Three heating members 23 may have the same structure. However, the present embodiment is not limited thereto and each of three heating members 23 may include a mutually different structure. Such a different structure may have, for example, a different length, a different thickness, and a different pitch, or may be made of a different material. In other words, some or all of the heating members 23 may have the same property or a different property. As in the first embodiment, the variable stiffness system 10 may include one heating member 23 and one driver 31 with respect to the entire variable stiffness device 20.

In the present embodiment, by means of the connecting member 25, it is possible to improve strength of the connecting portion of the shape-memory member 21, and to facilitate assembling of the variable stiffness device 20. Since the outer diameters of the connecting member 25 and the heating member 23 may substantially be the same as each other, the connecting strength of the connecting portion can be improved while the variable stiffness device 20 is kept thin as in the first embodiment. In the present embodiment, positioning of the heating member 23 can be achieved by the connecting member 25.

[First Modification]

Figure 4:
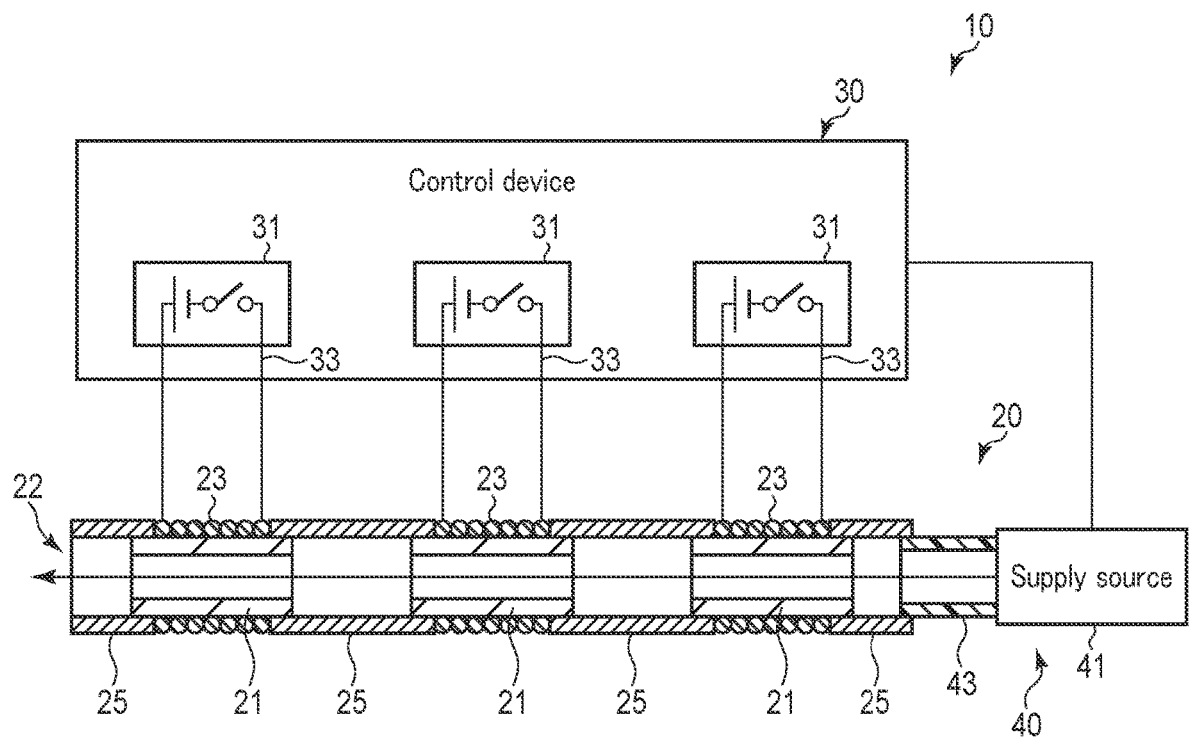
FIG. 4 is a schematic view of a first modification of the variable stiffness system according to the second embodiment.

A first modification of the second embodiment will now be described with reference to FIG. 4. FIG. 4 is a schematic view of the first modification of the variable stiffness system according to the second embodiment. In the present modification, differences in the modification from the second embodiment illustrated in FIG. 3 will be emphasized.

Adjacent ends of adjacent shape-memory members 21 are spaced apart from each other within the connecting member 25. Accordingly, in the longitudinal direction of the variable stiffness device 20, spaces are located between the ends of the shape-memory members 21. The length of the space is adjusted as necessary. As a result, the adjacent shape-memory members 21 are connected indirectly by the connecting member 25.

The conduit member 43 is inserted into an end of a connecting member 25. The end of the connecting member 25 may instead be inserted into the conduit member 43. The conduit member 43 directs fluid into the shape-memory member 21 through the inner space of the connecting member 25.

In the modification, it is possible to reduce the number of shape-memory members 21 or to reduce the length of the shape-memory member 21 with respect to the entire length of the shape-memory unit 22, which facilitates shaping of the shape-memory member 21.

[Second Modification]

Figure 5:
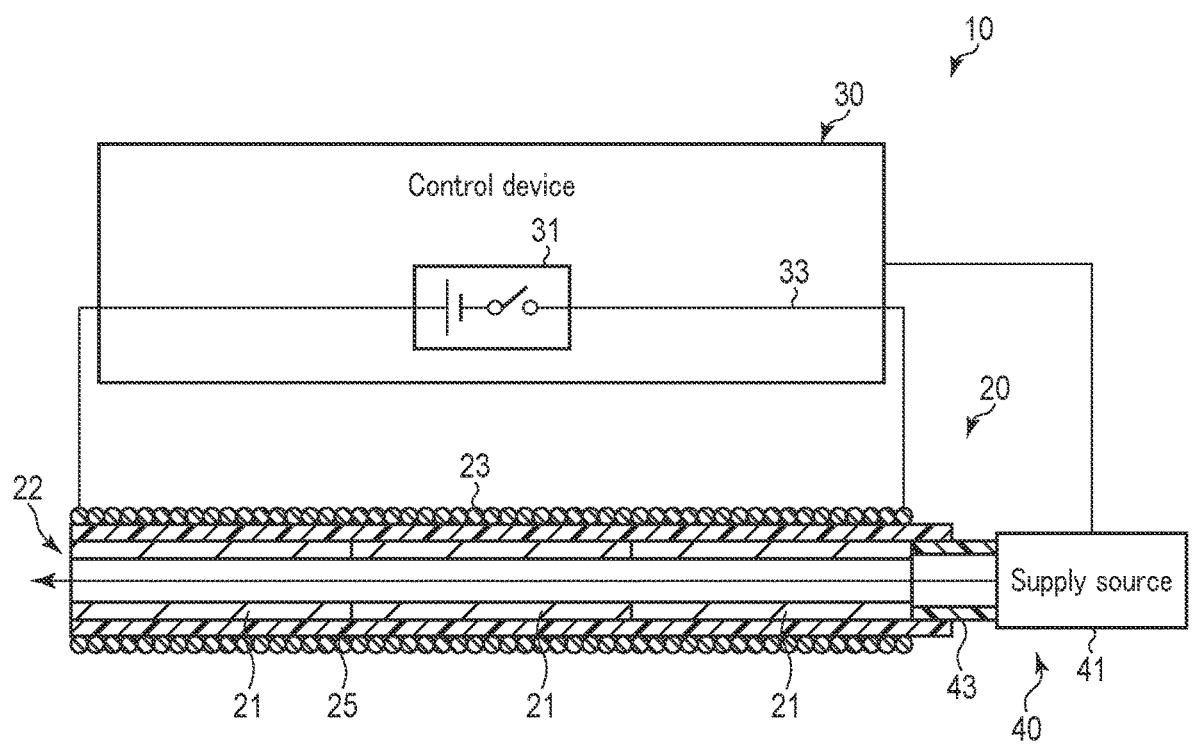
FIG. 5 is a schematic view of a second modification of the variable stiffness system according to the second embodiment.

A second modification of the second embodiment will now be described with reference to FIG. 5. FIG. 5 is a schematic view of the second modification of the variable stiffness system according to the second embodiment. In the present modification, differences in the modification from the second embodiment illustrated in FIG. 3 will be emphasized.

The connecting member 25 may, for example, be of a resin material. The connecting member 25 serves as a tube that has the same length as the entire length of the shape-memory unit 22. In the longitudinal direction of the variable stiffness device 20, adjacent shape-memory members 21 are located within the connecting member 25 along the entire length of the connecting member 25. The adjacent ends of adjacent shape-memory members 21 are arranged to come into contact with each other within the connecting member 25.

One heating member 23 is located along the entire length of the connecting member 25. One driver 31 is located in accordance with the one heating member 23. The heating member 23 is arranged around the outside of the connecting member 25. The heating member 23 extends spirally around the outer periphery of the connecting member 25 along the longitudinal axis of the connecting member 25. The heating member 23 is in close contact with the outer peripheral surface of the connecting member 25; however, the heating member 23 may be spaced apart from the outer peripheral surface of the connecting member 25 by a suitable clearance. Heat generated in the heating member 23 is transferred to the shape-memory member 21 through the connecting member 25. As in the second embodiment, three heating member 23 and three driver 31 may be arranged for the three shape-memory members 21, respectively.

In the modification, cooling fluid flowing in the shape-memory member 21 is prevented from leaking from a connecting portion of the shape-memory member 21 by means of the connecting member 25.

Third Embodiment

Figure 6:
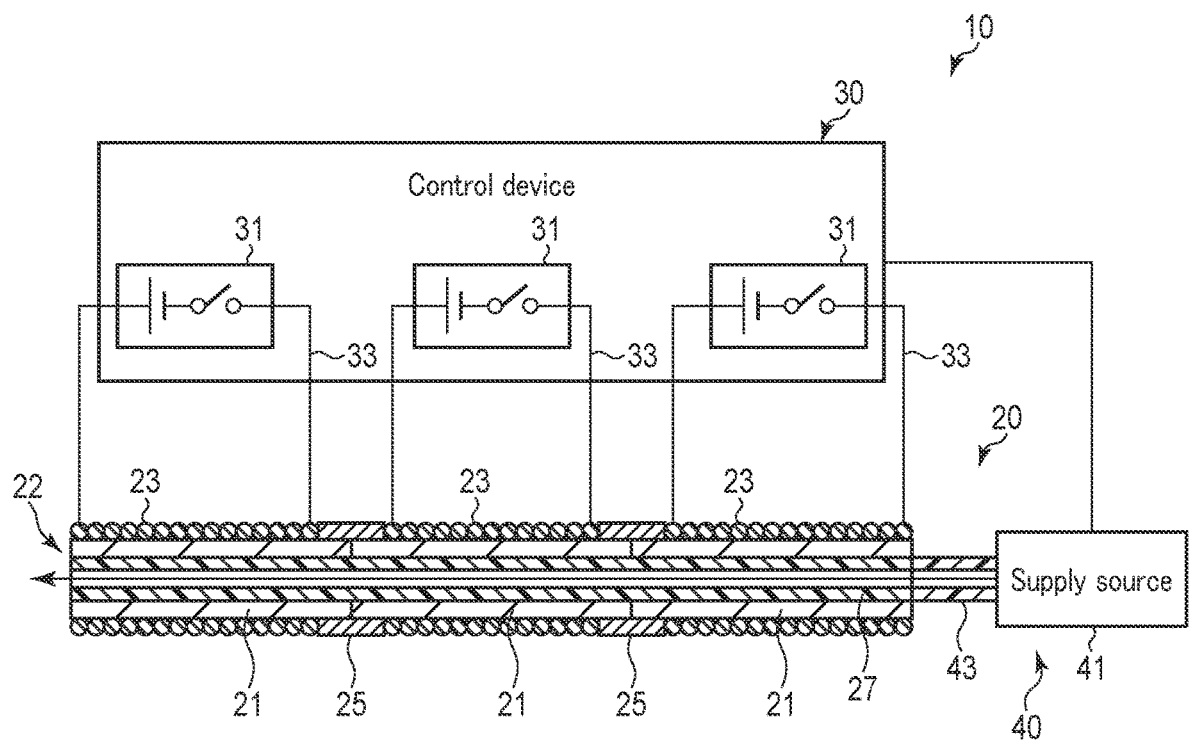
FIG. 6 is a schematic view of a variable stiffness system according to a third embodiment of the present invention.

A third embodiment of the present invention will now be described with reference to FIG. 6. FIG. 6 is a schematic view of a variable stiffness system according to the third embodiment. In the present embodiment, differences in the third embodiment from the second embodiment illustrated in FIG. 3 will be emphasized.

The shape-memory unit 22 includes a tubular member 27 connected to the conduit member 43. The tubular member 27 is located within the inner space of the shape-memory unit 22. The tubular member 27 is located along the entire length of the shape-memory unit 22 in the longitudinal direction of the variable stiffness device 20. The tubular member 27 may be longer than the entire length of the shape-memory unit 22. Accordingly, the end of the tubular member 27 opposite to the supply source 41 may protrude to the left in FIG. 6 from the shape-memory member 21 located on the leftmost side in FIG. 6. The outer peripheral surface of the tubular member 27 may be in contact with the inner peripheral surface of the shape-memory member 21. The tubular member 27 may, for example, be a tube made up of a resin material.

Fluid flows in the tubular member 27 from the supply source 41 through the conduit member 43. In the present embodiment, leakage of fluid from the connecting portion can be prevented by the tubular member 27.

It will be noted that the outer peripheral surface of the tubular member 27 may be joined to the inner peripheral surface of the shape-memory member 21, and the tubular member 27 may be located in the inner space of the shape-memory unit 22 so as to serve as an inner connecting member for connecting the shape-memory members 21 from inside of the shape-memory member 21. In this way, it is possible to improve connecting strength of the connecting portion of the shape-memory member 21 by means of the tubular member 27. The tubular member 27 may be integral with the conduit member 43.

[Modification]

Figure 7:
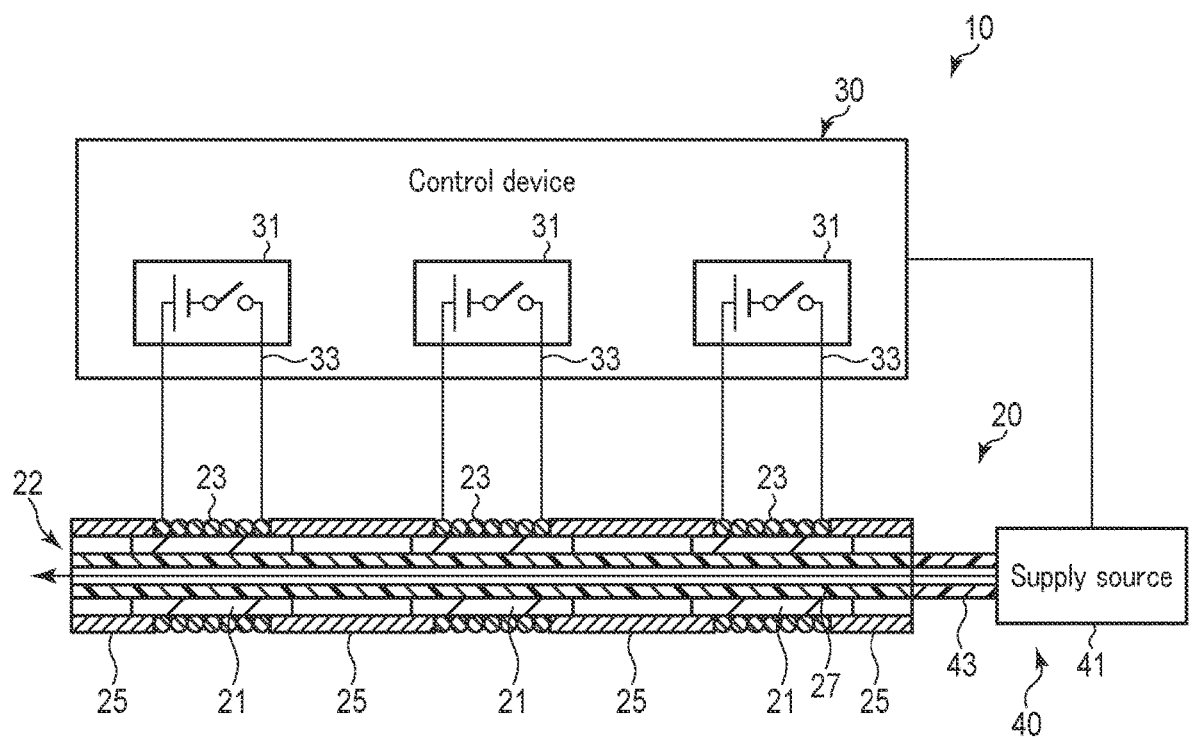
FIG. 7 is a schematic view of a modification of the variable stiffness system according to the third embodiment.

A modification of the third embodiment will now be described with reference to FIG. 7. FIG. 7 is a schematic view of the modification of the variable stiffness system according to the third embodiment. The modification is the configuration in the first modification according to the second embodiment illustrated in FIG. 4 combined with the tubular member 27 according to the third embodiment illustrated in FIG. 6.

In other words, the tubular member 27 is located inside the shape-memory members 21 and inside the connecting members 25 with adjacent ends of adjacent shape-memory members 21 being spaced apart from each other in the connecting members 25.

In the modification, fluid is not obstructed by steps formed by the inner peripheral surfaces of the connecting members 25 and ends of the shape-memory members 21, and the fluid can be smoothly supplied by the tubular member 27 in the shape-memory member 21.

Fourth Embodiment

Figure 8:
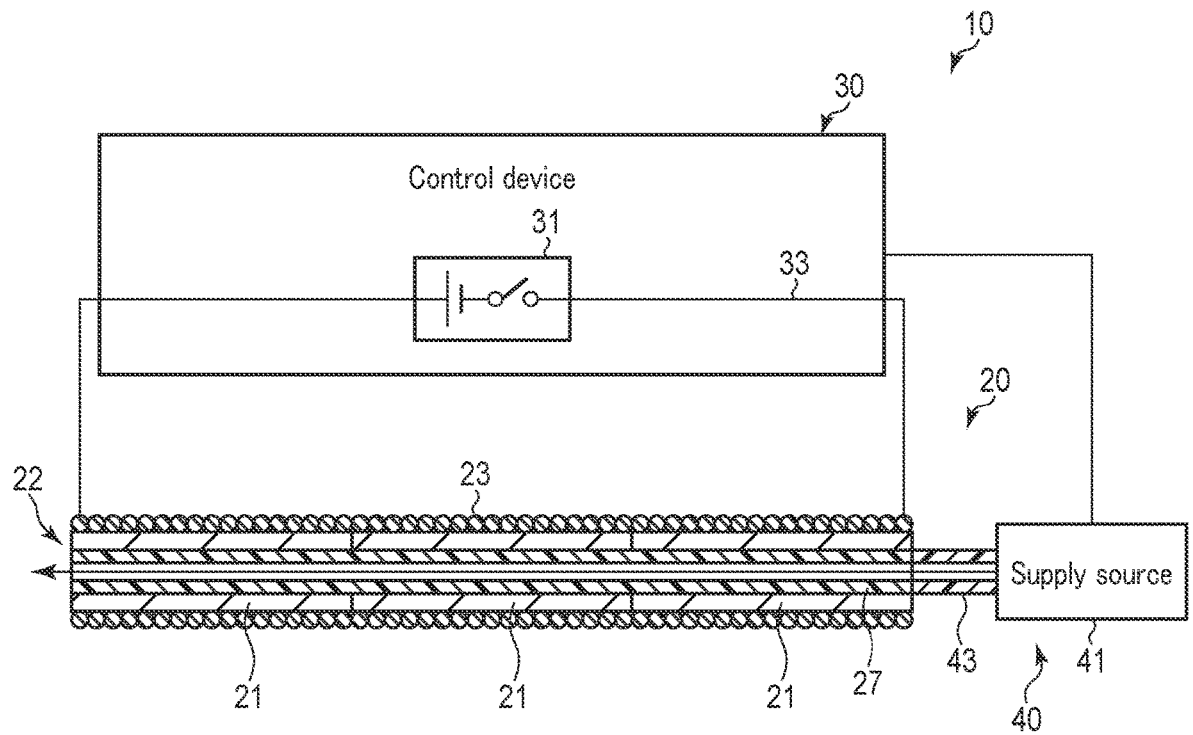
FIG. 8 is a schematic view of a variable stiffness system according to a fourth embodiment of the present invention.

A fourth embodiment of the present invention will now be described with reference to FIG. 8. FIG. 8 is a schematic view of a variable stiffness system according to the fourth embodiment. In the present embodiment, differences in the fourth embodiment from the third embodiment illustrated in FIG. 6 will be emphasized.

In the present embodiment, the connecting members 25 are omitted from the configuration of the third embodiment illustrated in FIG. 6, and the outer peripheral surface of the tubular member 27 is joined to the inner peripheral surfaces of the shape-memory members 21. The tubular member 27 is located in the inner space of the shape-memory unit 22 so as to serve as an inner connecting member for connecting the shape-memory members 21 from inside of the shape-memory member 21.

One heating member 23 is located along the entire length of the shape-memory unit 22. One driver 31 is located in accordance with the one heating member 23.

In the present embodiment, it is possible to omit the connecting members 25 and to reduce the number of components of the variable stiffness device 20.

Fifth Embodiment

Figure 9:
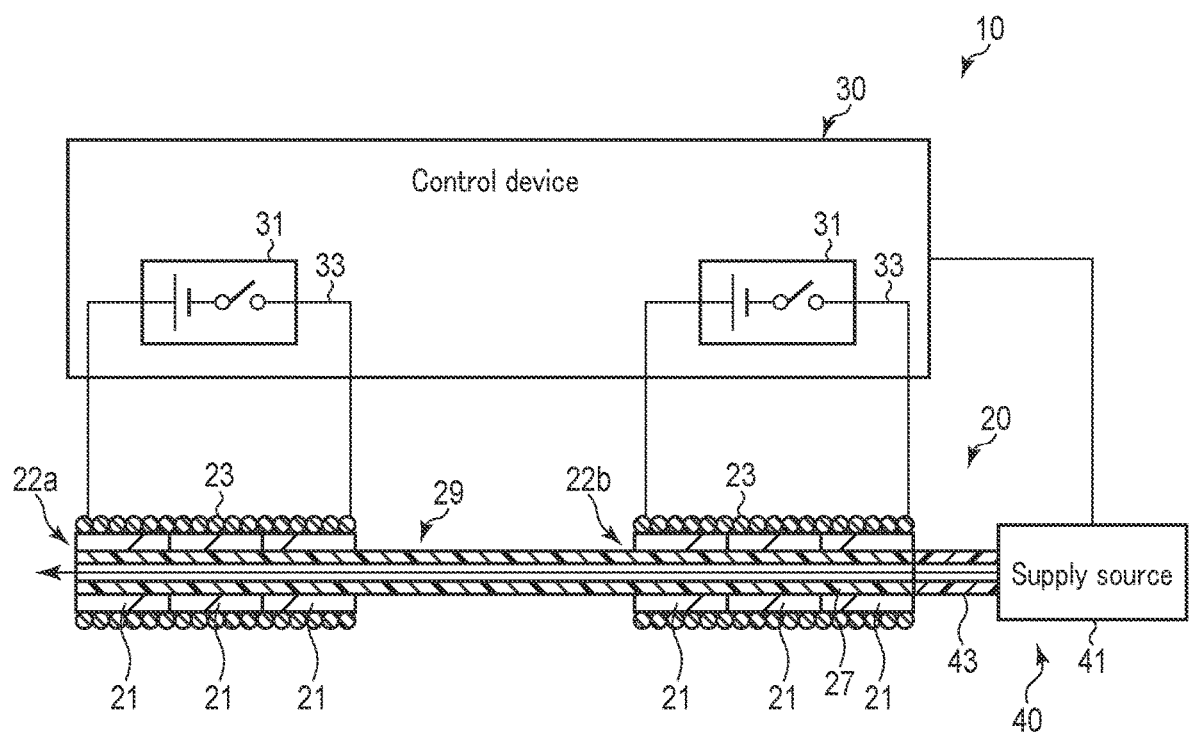
FIG. 9 is a schematic view of a variable stiffness system according to a fifth embodiment of the present invention.

A fifth embodiment of the present invention will now be described with reference to FIG. 9. FIG. 9 is a schematic view of a variable stiffness system according to the fifth embodiment. In the present embodiment, differences in the fifth embodiment from the fourth embodiment illustrated in FIG. 8 will be emphasized.

Although FIG. 9 illustrates an example in which two shape-memory units 22a, 22b are arranged for simplicity of illustration, there only needs to be two or more shape-memory units.

In each of the shape-memory units 22a, 22b, the shape-memory members 21 are connected by the tubular member 27 located in the shape-memory members 21. Ends of adjacent shape-memory units 22a, 22b in the longitudinal direction of the variable stiffness device 20 are spaced apart from each other. Accordingly, in the longitudinal direction of the variable stiffness device 20, a space 29 is located between the shape-memory units 22a, 22b. The length of the space 29 is adjusted as necessary.

One tubular member 27 extends from the inner space of the shape-memory unit 22b to the inner space of the shape-memory unit 22a so as to indirectly connect the shape-memory unit 22a and the shape-memory unit 22b.

In the present embodiment, since the shape-memory units 22a, 22b are located on two portions of the flexible member 101 spaced apart from each other, the stiffness of the two portions spaced apart from each other can rapidly be switched. In addition, the same stiffness of the portion in which the space 29 is located in the flexible member 101 as the stiffness of the tubular member 27 can be maintained.

Sixth Embodiment

A sixth embodiment of the present invention will now be described with reference to FIG. 10A. FIG. 10A is a schematic view of a variable stiffness system according to the sixth embodiment of the present invention. In FIG. 10A, members indicated by the like reference numerals as those in FIG. 1 are like members, and thus they will not be described in detail. In the present embodiment, differences in the sixth embodiment from other embodiments described above will be emphasized.

The variable stiffness device 20 further includes a first elongated member 50, a second elongated member 70 movable along the first elongated member 50, and moving mechanism 80 configured to move the second elongated member 70 with respect to the first elongated member 50. The first elongated member 50 is an outer cylinder, and the second elongated member 70 is a core located in the first elongated member 50. For example, the cross-sectional shape of the outer cylinder perpendicular to the longitudinal axis of the outer cylinder is an annular shape, and the outer periphery of the cross section of the core perpendicular to the longitudinal axis of the core has an annular shape. In this case, the variable stiffness device 20 provides stable stiffness against bends in any direction. The cross-sectional shapes of the outer cylinder and the core each may not be the annular shape, may be other shapes such as a C-shape.

In the present embodiment, the first elongated member 50 is, for example, positioned and fixed relative to the flexible member 101.

The first elongated member 50 includes at least one cylindrical hard member 51, at least one heating member 23, at least one heat insulation member 57 of a ring shape, and a hollow outer support member 55. Although FIG. 10A illustrates an example in which three hard members 51, two heating members 23, and four heat insulation members 57 are arranged for simplicity of illustration, there may be any number of the members.

The outer support member 55 is located inside the hard member 51, the heating member 23, and the heat insulation member 57. The outer support member 55 serves as a core member with respect to the hard member 51, the heating member 23, and the heat insulation member 57. The outer support member 55 is a cylindrical outer support member configured to support the hard member 51, the heating member 23, and the heat insulation member 57.

The outer support member 55 covers the second elongated member 70 over the entire length of the second elongated member 70. For example, the length of the outer support member 55 is substantially the same as the length of the second elongated member 70. The length of the outer support member 55 may be longer than the length of the second elongated member 70. The outer support member 55 is configured to guide, along the longitudinal direction of the first elongated member 50, the second elongated member 70 that moves with respect to the first elongated member 50 along the longitudinal direction of the first elongated member 50. The outer support member 55 is configured to be bendable.

The outer support member 55 includes, for example, a coil member such as a tightly-wound coil. The coil member of the outer support member 55 may be a loosely-wound coil. The outer support member 55 may be a soft tube or a cylindrical member formed of metal wires being twisted with each other. The outer support member 55 may include, for example, a wire-like and spiral metal member.

The hard member 51 is, for example, in a cylindrical shape. The hard member 51 includes, for example, a metal pipe. The hard member 51 is separate from the heating member 23 and the outer support member 55. The length of the hard member 51 is shorter than the length of the outer support member 55 and longer than the length of the heating member 23. The length of the hard member 51 may be the same as or shorter than the length of the heating member 23.

The inner peripheral surface of the hard member 51 is fixed to the outer peripheral surface of the outer support member 55 by, for example, bonding, welding, or the like. The hard member 51 is then positioned on the outer support member 55. The hard members 51 are not in direct contact with each other in the longitudinal direction of the first elongated member 50 and spaced apart from each other by a desired distance. In other words, the hard member 51 surrounds partially the outer support member 55 over the entire length of the outer support member 55. Accordingly, in the longitudinal direction of the first elongated member 50, there is a first space between the hard members 51. The heating member 23 is located in the first space, and the hard member 51 and the heating member 23 are alternately located on the outer peripheral surface of the outer support member 55 in the longitudinal direction of the first elongated member 50.

In the present embodiment, instead of the heating member 23 being wound around the outer support member 55 over the entire length of the outer support member 55, one heating member 23 is wound around a portion of the outer support member 55 in the entire length of the outer support member 55. In this way, the heating member 23 is partially wound around the outer support member 55.

The heating member 23 is positioned on the outer support member 55 by the hard members 51 in the longitudinal direction of the first elongated member 50. The outer diameter of the winding of the heating member 23 is substantially the same as the outer diameter of the hard member 51. Preferably, the winding of the heating member 23 does not protrude with respect to the hard member 51 in the direction perpendicular to the longitudinal axis of the first elongated member 50. The inner peripheral surface of the heating member 23 is in contact with the outer peripheral surface of the outer support member 55, and may be fixed to the outer peripheral surface of the outer support member 55. The inner peripheral surface of the heating member 23 may be separate from the outer peripheral surface of the outer support member 55.

With the hard member 51, the heating member 23, and the outer support member 55 as described above, the first elongated member 50 includes high bending stiffness sections 61 that have a relatively high bending stiffness, and low bending stiffness sections 63 that have a relatively low bending stiffness. In other words, the high bending stiffness section 61 is formed of the cylindrical hard member 51 and part of the outer support member 55 located in the hard member 51. The low bending stiffness section 63 is formed of the heating member 23 and part of the outer support member 55 located in the heating member 23. The outer support member 55 is included both the high bending stiffness section 61 and the low bending stiffness section 63.

The hard member 51 is harder than the heating member 23. The hard member 51 is a cylindrical hard portion that has a high bending stiffness, while the outer support member 55 and the heating member 23 are cylindrical soft portions that have a low bending stiffness.

As described above, the bending stiffness of the high bending stiffness section 61 is high, while the bending stiffness of the low bending stiffness section 63 is lower than the bending stiffness of the high bending stiffness section 61. Consequently, the first elongated member 50 is relatively less bendable in the high bending stiffness section 61 while relatively more bendable in the low bending stiffness section 63.

FIG. 10A illustrates an example in which three high bending stiffness sections 61 and two low bending stiffness sections 63 are arranged for simplicity of illustration.

The hard member 51 and the heating member 23 are alternately arranged. With the arrangement, the high bending stiffness sections 61 and the low bending stiffness sections 63 are alternately located in the longitudinal direction of the outer support member 55. Because of the length of the hard member 51 and the length of the heating member 23, the length of the high bending stiffness section 61 is longer than the length of the low bending stiffness section 63. The length of the high bending stiffness section 61 may be the same as or shorter than the length of the low bending stiffness section 63.

When the first elongated member 50 is fabricated, the outer support member 55 contributes to positioning of the hard member 51, definition of the distance between the hard members 51 (the length of the first space), and positioning of the heating member 23. In other words, the outer support member 55 brings an effect of facilitating positioning of the high bending stiffness section 61 and the low bending stiffness section 63 and definition of the length of each of the high bending stiffness section 61 and the low bending stiffness section 63. In addition, the outer support member 55 brings an effect of improving mechanical strength of the first elongated member 50.

Although the high bending stiffness sections 61 are located on opposite ends of the first elongated member 50 in FIG. 10A, the arrangement is not necessarily limited thereto. The low bending stiffness sections 63 may be located on opposite ends, or the high bending stiffness section 61 may be located on one end and the low bending stiffness section 63 may be located on the other end.

Since the first elongated member 50 is positioned and fixed relative to the flexible member 101, the low bending stiffness section 63 will be relatively positioned and fixed to a desired area of the flexible member 101.

The heat insulation member 57 may, for example, be of a resin material. The heat insulation member 57 is located between the hard member 51 and the heating member 23 in the longitudinal direction of the first elongated member 50. The heat insulation member 57 is fixed to an end of the hard member 51 by, for example, bonding, welding, or the like. Preferably, the heat insulation member 57 is in contact with the heating member 23. The heat insulation member 57 prevents heat generated by the heating member 23 from being transferred to the hard member 51.

The second elongated member 70 is located in the outer support member 55 and adjacent to the first elongated member 50.

The second elongated member 70 includes a hollow inner support member 75, at least one shape-memory unit 22, at least one soft member 73 that is softer than the shape-memory member 21 of the shape-memory unit 22, and a tubular member 27. FIG. 10A illustrates an example in which two shape-memory units 22 and three soft members 73 are arranged for simplicity of illustration, there may be any number of the members. The shape-memory unit 22 and the soft member 73 are located in the inner support member 75.

The inner support member 75 has a function of protecting the outer peripheral surface of the shape-memory unit 22 and the outer peripheral surface of the soft member 73 against the inner peripheral surface of the outer support member 55. The inner support member 75 is an intervening member that is interposed between the outer support member 55 and the shape-memory unit 22/the soft member 73 to prevent the shape-memory unit 22 and the soft member 73 from directly contacting with the outer support member 55. The inner support member 75 supports the shape-memory unit 22 and the soft member 73. The inner support member 75 is bendable.

The outer peripheral surface of the inner support member 75 is in contact with the inner peripheral surface of the outer support member 55, and the inner support member 75 is slid on the outer support member 55 by the moving mechanism 80. As long as the inner support member 75 is movable with respect to the outer support member 55, it may be configured that the outer peripheral surface of the inner support member 75 is not in contact with the inner peripheral surface of the outer support member 55, so that a space (not shown) is created between the outer peripheral surface of the inner support member 75 and the inner peripheral surface of the outer support member 55.

The inner support member 75 is, for example, in a cylindrical shape. The inner support member 75 includes, for example, a coil member such as a tightly-wound coil. The coil member of the inner support member 75 may be a loosely-wound coil. The inner support member 75 may be a soft tube or a cylindrical member formed of metal wires being twisted with each other. The inner support member 75 may include, for example, a wire-like and spiral metal member. The length of the inner support member 75 is substantially the same as the length of the low bending stiffness section 63.

The length of the shape-memory unit 22 is shorter than the inner support member 75. Preferably, the length of the shape-memory unit 22 is substantially the same as the length of the high bending stiffness section 61 and longer than the length of the low bending stiffness section 63.

The shape-memory units 22 are not in direct contact with each other in the longitudinal direction of the first elongated member 50 and spaced apart from each other by a desired distance in the longitudinal direction of the second elongated member 70. Accordingly, in the longitudinal direction of the second elongated member 70, a second space is located between the shape-memory units 22. A soft member 73 is located in the second space. Soft members 73 are also located on opposite ends of the second elongated member 70 in the longitudinal direction of the second elongated member 70. Accordingly, the shape-memory units 22 and the soft members 73 are alternately located in the longitudinal direction of the second elongated member 70, and arranged along the longitudinal direction of the second elongated member 70. The shape-memory units 22 and the soft members 73 are partially located in the inner support member 75 over the entire length of the inner support member 75.

An end of the soft member 73 comes into contact with an end of the shape-memory unit 22 adjacent to the end of the soft member 73. The end of the soft member 73 may be fixed to the end of the shape-memory unit 22 adjacent to the end of the soft member 73 by, for example, bonding, welding, or the like. The soft member 73 is provided for positioning of the shape-memory unit 22. In FIG. 10A, for example, the soft members 73 are located on opposite ends of the second elongated member 70. The outer peripheral surfaces of the soft members 73 located on the opposite ends are fixed to the inner peripheral surface of the inner support member 75 by, for example, bonding, welding, or the like. In this way, the soft member 73 excepting the soft members 73 located on the opposite ends and the shape-memory units 22 are positioned on the inner support member 75 without being fixed to the inner support member 75. As a matter of course, it may be configured that outer peripheral surfaces of the shape-memory units 22 and the soft member 73 are fixed to the inner peripheral surface of the inner support member 75 by, for example, bonding, welding, or the like, so that the shape-memory units 22 and the soft member 73 are positioned. If the shape-memory units 22 are fixed to the inner support member 75 by, for example, bonding, welding, or the like, the soft members 73 may be omitted.

Although the soft members 73 are located on the opposite ends of the second elongated member 70, the arrangement is not necessarily limited thereto. The shape-memory units 22 may be located on the opposite ends, or it may be that the soft member 73 is located on one end and the shape-memory unit 22 is located on the other end. If members located on the opposite ends are fixed to the inner support member 75 by, for example, bonding, welding, or the like, members located between the opposite ends may not be fixed to the inner support member 75.

The soft member 73 includes, for example, a spring member. The spring member includes, for example, a loosely-wound spring. The spring member may include, for example, a tightly-wound spring. The soft member 73 may include, for example, a string member such as a thin wire, or an elastic member such as rubber. The outer diameter of the winding of the soft member 73 is substantially the same as the outer diameter of the shape-memory unit 22. The soft member 73 is, for example, bendable. For example, the soft member 73 is softer and more bendable than the shape-memory unit 22. The length of the soft member 73 is shorter than the length of the shape-memory unit 22. Preferably, the length of the soft member 73 is substantially the same as the low bending stiffness section 63.

The shape-memory unit 22 is a hard portion that has a high bending stiffness, and the soft member 73 and the inner support member 75 are soft portions that have a low bending stiffness. Consequently, the second elongated member 70 is relatively less bendable in the shape-memory unit 22 while relatively more bendable in the soft member 73.

When the second elongated member 70 is fabricated, the inner support member 75 contributes, for example, to positioning of the shape-memory unit 22 and the soft member 73, and definition of the distance between the shape-memory units 22. In addition, the inner support member 75 brings an effect of improving mechanical strength of the second elongated member 70.

For example, when the phase of the shape-memory unit 22 is the first phase, the bending stiffness of the shape-memory unit 22 is lower than the bending stiffness of the high bending stiffness section 61, and is substantially the same as or lower than the bending stiffness of the low bending stiffness section 63. When the phase of the shape-memory unit 22 is the second phase, the bending stiffness of the shape-memory unit 22 is substantially the same as or lower than the bending stiffness of the high bending stiffness section 61, and is higher than the bending stiffness of the low bending stiffness section 63. When the phase of the shape-memory unit 22 is the second phase, the bending stiffness of the shape-memory unit 22 may be higher than the bending stiffness of the high bending stiffness section 61. The bending stiffness of the shape-memory unit 22 may be higher or lower than the bending stiffness of both the soft member 73 and the inner support member 75 regardless of whether the phase of the shape-memory unit 22 is the first phase or the second phase. The soft member 73 is softer than the low bending stiffness section 63.

In the present embodiment, the tubular member 27 is located in the inner space of the shape-memory unit 22 and inside the winding of the soft member 73. The outer peripheral surface of the tubular member 27 is in contact with the inner peripheral surface of the shape-memory unit 22 and the inner peripheral surface of the soft member 73. Such a configuration leads to a thinner variable stiffness device 20. The inner peripheral surface of the shape-memory unit 22 and the inner peripheral surface of the soft member 73 may be spaced apart from the outer peripheral surface of the tubular member 27 by a suitable clearance, or may be in close contact with the outer peripheral surface of the tubular member 27.

The second elongated member 70 moves in the outer support member 55 along the longitudinal direction of the outer support member 55 so as to change the position of the second elongated member 70 with respect to the first elongated member 50. The relative position between the first elongated member 50 and the second elongated member 70 and the phase of the shape-memory unit 22 vary, and thus the stiffness of part of the variable stiffness device 20 varies in the longitudinal direction of the variable stiffness device 20. In this way, the variable stiffness device 20 provides the flexible member 101 with different levels of stiffness.

When the second elongated member 70 moves for the variation in the relative position, the outer peripheral surface of the inner support member 75 slides on the inner peripheral surface of the outer support member 55. The moving mechanism 80 pulls or pushes the second elongated member 70 to move the second elongated member 70. For example, the inner support member 75 is pulled or pushed. The moving mechanism 80 is electrically connected to the control device 30, and drive of the moving mechanism 80, that is, the movement of the second elongated member 70 caused by the moving mechanism 80 is controlled by the control device 30.

The moving mechanism 80 includes, for example, a motor (not shown) and a moving member (not shown) connected to an end of the second elongated member 70 and configured to move the second elongated member 70 by a rotational force of the motor. The motor may be driven by operating the switch 103a (see FIG. 1) on the control section 103 to turn on or off. The moving member is, for example, directly connected to an end of the inner support member 75 and pulls or pushes the second elongated member 70 by means of the rotational force of the motor. In this case, the inner support member 75 moves along with the shape-memory unit 22 and the soft member 73 that are fixed to the inner support member 75. During the movement, since the tubular member 27 is immovable and fixed inside the flexible member 101, the moving shape-memory unit 22 and soft member 73 slide on the tubular member 27. The moving member is located from a position where the motor is located to an end of the inner support member 75. For example, the moving member is located in the control section 103 and the flexible member 101. The moving member is, for example, a wire-like member. In this way, the moving mechanism 80 is electrically operated.

The control device 30 controls the motor of the moving mechanism 80 to move the second elongated member 70. In response to the operation of the switch 103a, the control device 30 controls the moving mechanism 80 to cause pulling and pushing and to stop.

It may be configured that the motor is omitted and the second elongated member 70 is manually operated as the moving mechanism 80. For example, the moving mechanism 80 may include the control dial 103c (see FIG. 1) instead of the motor. The control dial 103c is connected to the moving member. For example, the control dial 103c is operated by fingers gripping the control section 103 and rotated by the operation around the central axis of the control dial 103c. The control dial 103c is switched to on or off positions by the rotation. In response to the switching, the moving member is pulled or pushed. In this way, the second elongated member 70 moves. Instead of the control dial 103c, a lever (not shown) may be used. In this way, the moving mechanism 80 is manually operated. In this case, the control device 30 is omitted.

Further, it may be configured that the moving mechanism 80 and the control device 30 are omitted, and the second elongated member 70 is moved by an operator manually operating the variable stiffness device 20. For example, an end of the second elongated member 70 is held by the operator by hand, and the second elongated member 70 is pushed or pulled by the operator to move. Preferably, for holdings, the second elongated member 70 is longer than the first elongated member 50 and an end of the second elongated member 70 protrudes from the first elongated member 50 to the outside in the longitudinal direction of the second elongated member 70. As described later, when the first elongated member 50 and the second elongated member 70 are located in the cylindrical flexible member 101, for example, the end of the second elongated member 70 extends to the control section 103 and, for holdings, the end of the second elongated member 70 protrudes from the inside of the control section 103 through an enclosure portion of the control section 103 to the outside of the control section 103. The end of the second elongated member 70 may protrude at the proximal end of the flexible member 101. Further, regardless of the end of the second elongated member 70, any portion to be held by the operator may protrude to the outside.

FIG. 10A also illustrates the variable stiffness device 20 being in a lowest stiffness state (super-soft state). In the lowest stiffness state, the variable stiffness system 10 is in the initial state, the driver 31 does not supply an electric current to the heating member 23, the heating member 23 does not generate heat, the phase of the shape-memory unit 22 is the first phase, and the shape-memory unit 22 is in the low stiffness state. In the lowest stiffness state, the supply source 41 does not supply fluid.

In the lowest stiffness state, the shape-memory unit 22 in the low stiffness state is located in the high bending stiffness section 61 that is the hard portion and the soft member 73 is located in the low bending stiffness section 63 that is the soft portion. The low bending stiffness section 63 is in the most bendable state and the variable stiffness device 20 provides the flexible member 101 with the lowest level of stiffness in which the flexible member 101 is bendable. Then, the first elongated member 50, the second elongated member 70, and the flexible member 101 can be bent in the easiest way by, for example, an external force.

As illustrated in FIG. 10B, when the variable stiffness device 20 is switched from the lowest stiffness state to the low stiffness state (soft state), only the second elongated member 70 is moved by the moving mechanism 80 with respect to the lowest stiffness state as illustrated in FIG. 10A. Accordingly, in the low stiffness state, the driver 31 does not supply an electric current to the heating member 23, the heating member 23 does not generate heat, the phase of the shape-memory unit 22 is the first phase, and the supply source 41 does not supply fluid.

In the low stiffness state, the shape-memory unit 22 in the low stiffness state in which the shape-memory unit 22 is harder than the soft member 73 is located in the low bending stiffness section 63, and the low bending stiffness section 63 is less bendable than in the lowest stiffness state. Accordingly, the variable stiffness device 20 provides the flexible member 101 with a relatively low level of stiffness in which the flexible member 101 is bendable. The first elongated member 50, the second elongated member 70, and the flexible member 101 are, for example, less bendable than in the lowest stiffness state.

As illustrated in FIG. 10C, when the variable stiffness device 20 is switched from the low stiffness state to the high stiffness state (hard state), the second elongated member 70 is not moved with respect to the low stiffness state as illustrated in FIG. 10B. In the high stiffness state, the driver 31 supplies an electric current to the heating member 23 and the heating member 23 generates heat. The supply source 41 does not supply fluid.

In the high stiffness state, the shape-memory unit 22 is heated by heat generated by the heating member 23, and the phase of the shape-memory unit 22 is switched from the first phase to the second phase by the heat. In this way, the shape-memory unit 22 varies from the low stiffness state to the high stiffness state. The shape-memory unit 22 in the high stiffness state is indicated by solid black in FIG. 10C.

The shape-memory unit 22 in the high stiffness state is located in the low bending stiffness section 63 that is the soft portion and the low bending stiffness section 63 is in a state in which it is less bendable than in the low stiffness state. Accordingly, the variable stiffness device 20 provides the flexible member 101 with a relatively high level of stiffness in which the flexible member 101 is less bendable. A less-bendable shape may, for example, be linear. The first elongated member 50, the second elongated member 70, and the flexible member 101 can maintain, for example, a substantially linear state, or can be less bendable by an external force than in the low stiffness state.

In FIG. 10C, although two shape-memory units 22 are in the high stiffness state, this is not necessarily a limitation. One shape-memory unit 22 selected from the two shape-memory units 22 may be in the high stiffness state. The thermal conductivity of the soft member 73 is lower than the thermal conductivity of the shape-memory unit 22. Accordingly, heat transfer from a heated shape-memory unit 22 to another unheated shape-memory unit 22 through the soft member 73 is suppressed.

Figure 10D:
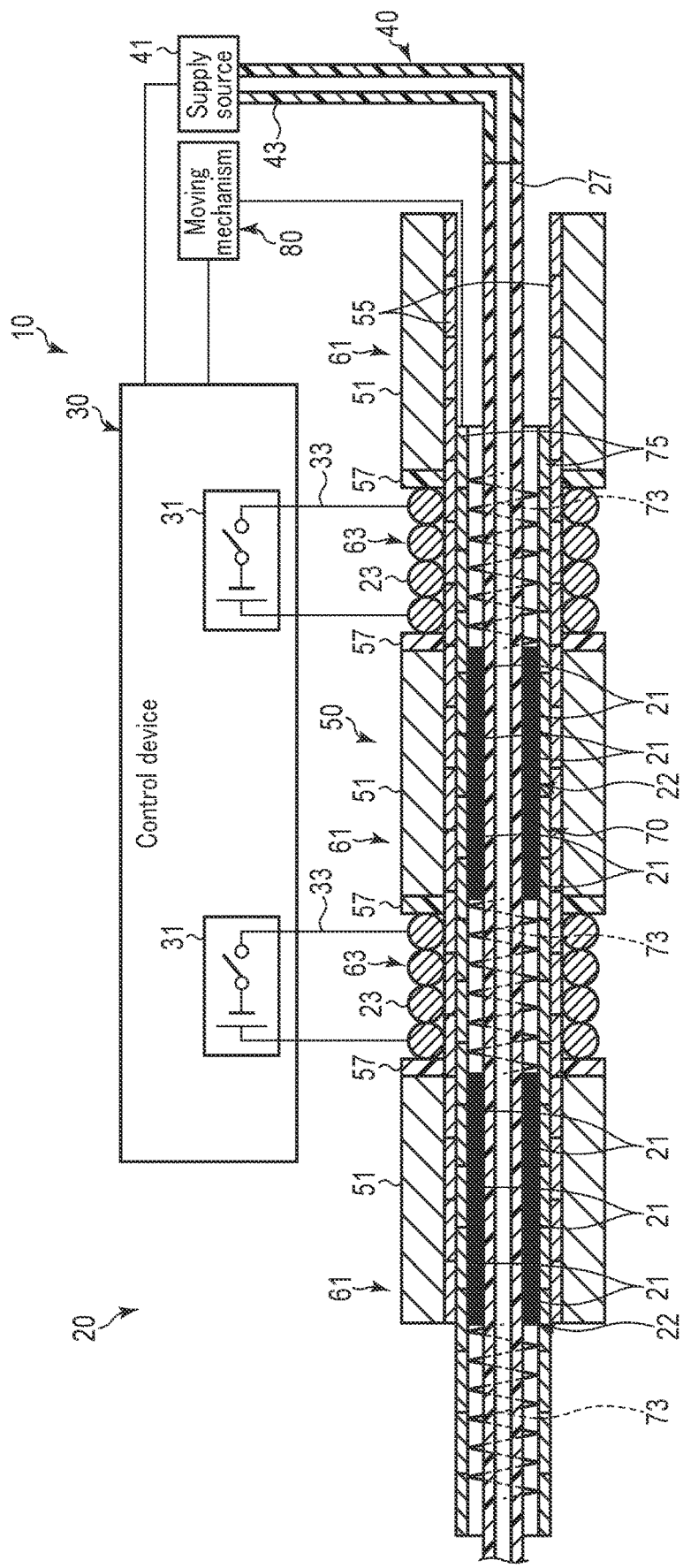
FIG. 10D illustrates that the variable stiffness device illustrated in FIG. 10C is switched to a first state of returning states representing the process of returning from the high stiffness state to the lowest stiffness state.
Figure 10E:
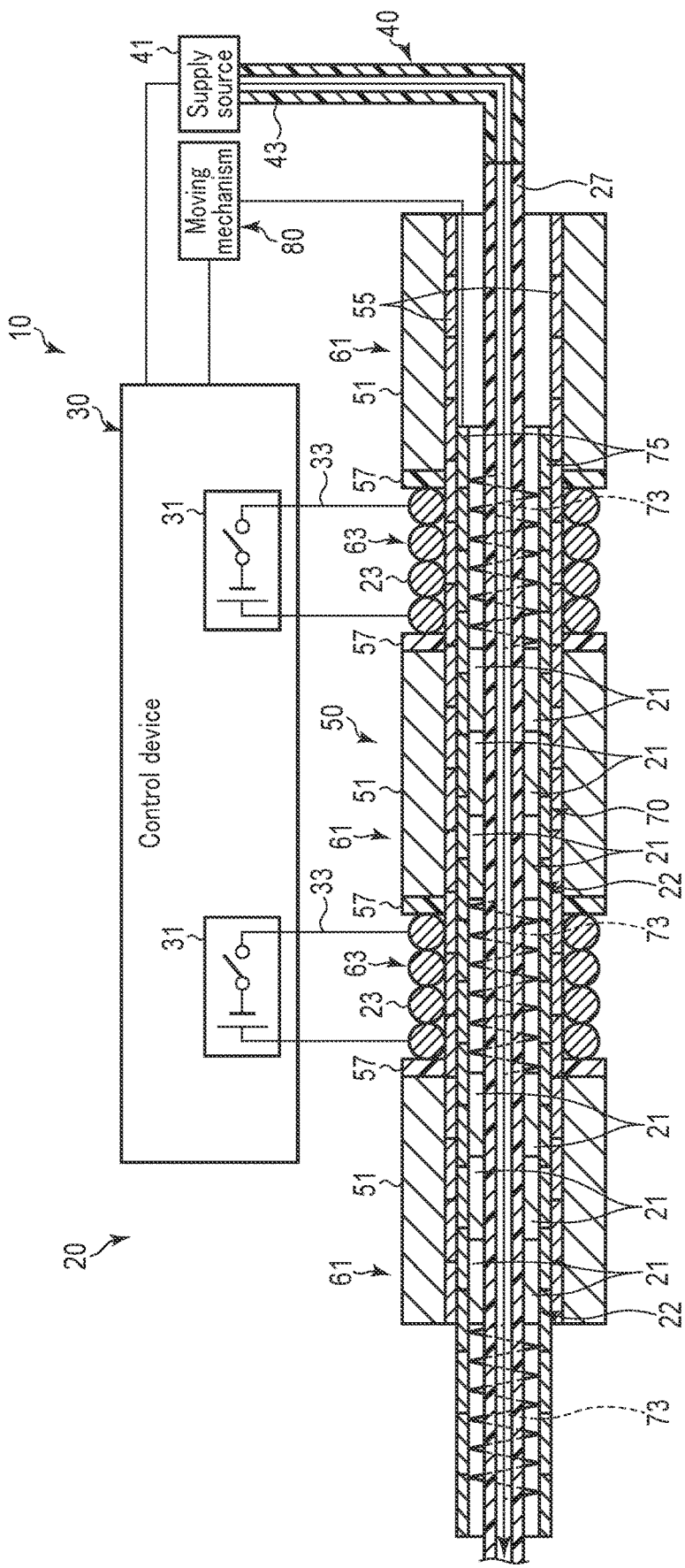
FIG. 10E illustrates that the variable stiffness device illustrated in FIG. 10D is switched from the first state to a second state of the returning states.

The variable stiffness device 20 is returned from the high stiffness state illustrated in FIG. 10C to the lowest stiffness state illustrated in FIG. 10A as illustrated in FIG. 10D and FIG. 10E. FIG. 10D and FIG. 10E illustrate the variable stiffness device 20 being in a returning state representing the process of returning from the high stiffness state to the lowest stiffness state. The returning state includes a first returning state illustrated in FIG. 10D and a second returning state illustrated in FIG. 10E. The second returning state follows the first returning state.

In the first returning state, the second elongated member 70 is moved by the moving mechanism 80 with respect to the high stiffness state as illustrated in FIG. 10C, for example. The driver 31 stops supplying the electric current to the heating member 23 and the heating member 23 stops generating heat. The supply source 41 may supply fluid.

In the first returning state, the shape-memory unit 22 in the high stiffness state is located in the high bending stiffness section 61, and the soft member 73 is located in the low bending stiffness section 63 that is the soft portion. Accordingly, the low bending stiffness section 63 is in the most bendable state, and the variable stiffness device 20 provides the flexible member 101 with the lowest level of stiffness. In this case, the shape-memory unit 22 in the high stiffness state is moved by the moving mechanism 80 from the low bending stiffness section 63 to the high bending stiffness section 61. Accordingly, in the first state, without waiting for a decrease in the temperature of the shape-memory unit 22 in the high stiffness state, it is possible to switch the variable stiffness device 20 from the high stiffness state to the lowest stiffness state rapidly.

In the second returning state, the second elongated member 70 is not moved by the moving mechanism 80 with respect to the first returning state as illustrated in FIG. 10D, for example. The driver 31 does not supply an electric current to the heating member 23 and the heating member 23 does not generate heat. The supply source 41 supplies fluid.

The fluid flowing out of the supply source 41 passes through the inner space of the conduit member 43 and the inner space of the tubular member 27 as indicated by an arrow in FIG. 10E. The heat in the shape-memory unit 22 is transferred to the fluid through the tubular member 27, and passes through inner space of the tubular member 27 with the fluid. In this way, the cooling system 40 supplies fluid to the inner space of the tubular member 27 to cool the shape-memory unit 22 to a desired temperature. The desired temperature refers for example to a temperature at which the phase of the shape-memory unit 22 becomes the first phase.

Accordingly, in the second returning state, the shape-memory unit 22 in the high stiffness state is cooled by the fluid into the low stiffness state. Then, the second returning state varies to the lowest stiffness state illustrated in FIG. 10A. In the second returning state, the shape-memory unit 22 is cooled more rapidly than natural cooling and can return rapidly to the low stiffness state. In the second state, the transition from the lowest stiffness state that is the initial state to the low stiffness state, and thus redriving of the variable stiffness device 20 can be facilitated.

As described above, in the present embodiment, the response to switching of the stiffness in a desired area in the flexible member 101 can be improved and the variability of the stiffness can precisely be controlled.

Note that the invention of the present application is not limited to the above embodiments and can be variously modified in a range not departing from the gist in an implementation stage. In addition, the embodiments may be implemented in appropriate combinations as much as possible, and in that case, combined effects are obtained. Furthermore, the above embodiments include inventions at various stages, and various inventions can be extracted by appropriate combinations of plural constituent elements disclosed.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A variable stiffness device comprising:
a shape-memory unit formed of at least two hollow shape-memory members connected together, each of the shape-memory members being transitionable in phase between a first phase in which the shape-memory member is in a low stiffness state and a second phase in which the shape-memory member is in a high stiffness state, the shape-memory member in the high stiffness state having a higher level of stiffness than in the low stiffness state, hollow portions of the shape-memory members being connected together so that the shape-memory unit has a lumen-like inner space configured to allow fluid for cooling the shape-memory members to flow; and
a heating material configured to transfer heat to the shape-memory unit to heat the shape-memory members.

2. The variable stiffness device according to claim 1, wherein
the shape-memory unit includes a cylindrical connecting member, and
the connecting member is located outside of the shape-memory members to connect the shape-memory members together.

3. The variable stiffness device according to claim 2, wherein
adjacent shape-memory members of the shape-memory members are spaced apart from each other.

4. The variable stiffness device according to claim 2, wherein
the shape-memory unit includes a tubular member, and
the tubular member is located in the inner space and the tubular member is configured to allow the fluid to flow therein.

5. The variable stiffness device according to claim 1, wherein the inner space is configured such that the fluid flows in the inner space while the fluid is in contact with inner peripheral surfaces of the shape-memory members.

6. The variable stiffness device according to claim 1, wherein adjacent shape-memory members of the shape-memory members are arranged to come into contact with each other.

7. The variable stiffness device according to claim 4, wherein the tubular member connects the shape-memory members from inside of the shape-memory members.

8. The variable stiffness device according to claim 1, wherein
the shape-memory unit includes a tubular member, and the tubular member is located in the inner space, the tubular member is configured to allow the fluid to flow therein, the tubular member connecting the shape-memory members from inside of the shape-memory members.

9. The variable stiffness device according to claim 8, wherein
adjacent shape-memory members of the shape-memory members are arranged to come into contact with each other.

10. The variable stiffness device according to claim 8, wherein
adjacent shape-memory members of the shape-memory members are spaced apart from each other.

11. The variable stiffness device according to claim 1, wherein the heating material is arranged around outside of the shape-memory members.

12. The variable stiffness device according to claim 1, wherein each of the shape-memory members comprises a shape memory alloy.

13. A variable stiffness system, comprising:
the variable stiffness device according to claim 1;
a control device configured to control the heating material for heating; and
a cooling system configured to supply the fluid to the shape-memory unit.

14. An endoscope, comprising:
the variable stiffness device according to claim 1; and
a flexible member in which the variable stiffness device is installed.

* * * * *